United States Patent
Cabiri

(10) Patent No.: US 10,668,213 B2
(45) Date of Patent: Jun. 2, 2020

(54) MOTION ACTIVATED MECHANISMS FOR A DRUG DELIVERY DEVICE

(71) Applicant: MEDIMOP Medical Projects Ltd., Ra'anana (IL)

(72) Inventor: Oz Cabiri, Macabim-Reut (IL)

(73) Assignee: West Pharma. Services IL, Ltd., Ra'anana (IL)

( * ) Notice: Subject to any disclaimer, the term of this patent is extended or adjusted under 35 U.S.C. 154(b) by 359 days.

(21) Appl. No.: 15/750,791

(22) PCT Filed: Mar. 14, 2013

(86) PCT No.: PCT/US2013/031598
§ 371 (c)(1),
(2) Date: Feb. 6, 2018

(87) PCT Pub. No.: WO2013/148270
PCT Pub. Date: Oct. 3, 2013

(65) Prior Publication Data
US 2019/0167899 A1 Jun. 6, 2019

Related U.S. Application Data

(63) Continuation-in-part of application No. 13/429,942, filed on Mar. 26, 2012, now Pat. No. 9,463,280.

(51) Int. Cl.
*A61M 31/00* (2006.01)
*A61M 5/172* (2006.01)
(Continued)

(52) U.S. Cl.
CPC ........ *A61M 5/172* (2013.01); *A61M 5/14248* (2013.01); *A61M 5/14566* (2013.01);
(Continued)

(58) Field of Classification Search
CPC .............. A61M 5/14248; A61M 5/172; A61M 2005/1402; A61M 2005/14208;
(Continued)

(56) References Cited

U.S. PATENT DOCUMENTS 3,946,732 A 3/1976 Hurscham
3,994,295 A 11/1976 Wulff
(Continued)

FOREIGN PATENT DOCUMENTS

CN 101703816 A 5/2010
CN 101868273 A 10/2010
(Continued)

OTHER PUBLICATIONS

U.S. Appl. No. 13/429,942 by Cabiri, filed Mar. 26, 2012.
(Continued)

*Primary Examiner* — Rebecca E Eisenberg
(74) *Attorney, Agent, or Firm* — Panitch Schwarze Belisario & Nadel LLP

(57) ABSTRACT

A method and apparatus are disclosed for delivery of a drug to a recipient. In some embodiments, the delivery apparatus may include a mechanical drive train. Motion of the drive train may drive priming of the device. Subsequently motion of the drive train may discharge the drug. The priming may include unsealing a drug reservoir and/or locking a door. In some embodiments, the rate of discharging may be controlled and/or adjustable. Optionally the apparatus may be disposable. Optionally, the apparatus may have a base that is attachable to the recipient. Optionally, motion of the drive train may be parallel to the base of the apparatus. Optionally, the apparatus may release a hypodermic needle into the recipient. Optionally, release of the hypodermic needle may be in a direction non-parallel and/or orthogonal to the motion of the drive train.

17 Claims, 21 Drawing Sheets

(51) Int. Cl.
*A61M 5/145* (2006.01)
*A61M 5/162* (2006.01)
*A61M 5/142* (2006.01)
A61M 5/24 (2006.01)
A61M 5/158 (2006.01)
A61M 5/14 (2006.01)

(52) U.S. Cl.
CPC ..... *A61M 5/162* (2013.01); *A61M 2005/1402* (2013.01); *A61M 2005/14208* (2013.01); *A61M 2005/14256* (2013.01); *A61M 2005/1581* (2013.01); *A61M 2005/247* (2013.01)

(58) Field of Classification Search
CPC .......... A61M 2005/14256; A61M 2005/1581; A61M 2005/247; A61M 5/14566; A61M 5/162; A61M 2005/14268; A61M 2005/14533; A61M 2005/14573; A61M 2005/2474; A61M 2205/123; A61M 5/14244; A61M 5/1452; A61M 5/3146; A61M 5/46
See application file for complete search history.

(56) References Cited

U.S. PATENT DOCUMENTS

| | | |
|---|---|---|
| 4,167,663 A | 9/1979 | Granzow, Jr. et al. |
| 4,273,122 A | 6/1981 | Whitney et al. |
| 4,396,385 A | 8/1983 | Kelly et al. |
| 4,601,702 A | 7/1986 | Ludson |
| 4,634,426 A | 1/1987 | Kamen |
| 4,886,499 A | 12/1989 | Cirelli et al. |
| 4,908,014 A | 3/1990 | Kroyer |
| 4,919,596 A | 4/1990 | Slate et al. |
| 4,950,235 A | 8/1990 | Slate et al. |
| 4,950,246 A | 8/1990 | Muller |
| 5,109,850 A | 5/1992 | Blanco et al. |
| 5,131,816 A | 7/1992 | Brown et al. |
| 5,254,096 A | 10/1993 | Rondelet et al. |
| 5,342,313 A | 8/1994 | Campbell et al. |
| 5,354,287 A | 10/1994 | Wacks |
| 5,383,865 A | 1/1995 | Michel |
| 5,411,482 A | 5/1995 | Campbell |
| 5,501,665 A | 3/1996 | Jhuboo et al. |
| 5,558,639 A | 9/1996 | Gangemi et al. |
| 5,593,390 A | 1/1997 | Castellano et al. |
| 5,616,132 A | 4/1997 | Newman |
| 5,643,218 A | 7/1997 | Lynn et al. |
| 5,647,853 A | 7/1997 | Feldmann et al. |
| 5,658,133 A | 8/1997 | Anderson et al. |
| 5,690,618 A | 11/1997 | Smith et al. |
| D393,314 S | 4/1998 | Meisner et al. |
| 5,800,420 A | 9/1998 | Gross et al. |
| 5,807,375 A | 9/1998 | Gross et al. |
| 5,814,020 A | 9/1998 | Gross |
| 5,851,197 A | 12/1998 | Marano et al. |
| 5,858,001 A | 1/1999 | Tsals et al. |
| 5,858,008 A | 1/1999 | Capaccio |
| 5,931,814 A | 8/1999 | Alex et al. |
| 5,957,895 A | 9/1999 | Sage et al. |
| 5,993,423 A | 11/1999 | Choi |
| 5,997,501 A | 12/1999 | Gross et al. |
| 6,004,297 A | 12/1999 | Steenfeldt-Jensen et al. |
| 6,039,713 A | 3/2000 | Botich et al. |
| 6,064,797 A | 5/2000 | Crittendon et al. |
| 6,074,369 A | 6/2000 | Sage et al. |
| 6,175,688 B1 | 1/2001 | Cassidy et al. |
| 6,186,982 B1 | 2/2001 | Gross et al. |
| 6,200,289 B1 | 3/2001 | Hochman et al. |
| 6,248,093 B1 | 6/2001 | Moberg |
| 6,277,095 B1 | 8/2001 | Kriesel et al. |
| 6,277,098 B1 | 8/2001 | Klitmose et al. |
| 6,277,099 B1 | 8/2001 | Strowe et al. |
| 6,287,283 B1 | 9/2001 | Ljunggreen et al. |
| 6,362,591 B1 | 3/2002 | Moberg |
| 6,391,005 B1 | 5/2002 | Lum et al. |
| 6,423,029 B1 | 7/2002 | Elsberry |
| 6,423,035 B1 | 7/2002 | Das et al. |
| D465,026 S | 10/2002 | May et al. |
| 6,458,102 B1 | 10/2002 | Mann et al. |
| 6,485,461 B1 | 11/2002 | Mason et al. |
| 6,485,465 B2 | 11/2002 | Moberg et al. |
| 6,500,150 B1 | 12/2002 | Gross et al. |
| 6,517,517 B1 | 2/2003 | Farrugia et al. |
| D471,274 S | 3/2003 | Diaz et al. |
| D471,983 S | 3/2003 | Hippolyte et al. |
| 6,530,901 B1 | 3/2003 | Tsukada et al. |
| 6,555,986 B2 | 4/2003 | Moberg |
| 6,558,351 B1 | 5/2003 | Steil et al. |
| 6,589,229 B1 | 7/2003 | Connelly et al. |
| 6,595,956 B1 | 7/2003 | Gross et al. |
| 6,595,960 B2 | 7/2003 | West et al. |
| 6,645,181 B1 | 11/2003 | Lavi et al. |
| 6,652,482 B2 | 11/2003 | Hochman |
| 6,656,158 B2 | 12/2003 | Mahoney et al. |
| 6,656,159 B2 | 12/2003 | Flaherty |
| 6,659,980 B2 | 12/2003 | Moberg et al. |
| 6,673,033 B1 | 1/2004 | Sciulli et al. |
| 6,679,862 B2 | 1/2004 | Diaz et al. |
| 6,699,218 B2 | 3/2004 | Flaherty et al. |
| 6,749,587 B2 | 6/2004 | Flaherty |
| 6,768,425 B2 | 7/2004 | Flaherty et al. |
| 6,786,890 B2 | 9/2004 | Preuthun et al. |
| 6,800,071 B1 | 10/2004 | McConnell et al. |
| 6,805,687 B2 | 10/2004 | Dextradeur et al. |
| 6,824,529 B2 | 11/2004 | Gross et al. |
| 6,830,558 B2 | 12/2004 | Flaherty et al. |
| 6,843,782 B2 | 1/2005 | Gross et al. |
| 6,854,620 B2 | 2/2005 | Ramey |
| 6,905,298 B1 | 6/2005 | Haring |
| 6,908,452 B2 | 6/2005 | Diaz et al. |
| 6,933,693 B2 | 8/2005 | Schuchmann |
| 6,950,028 B2 | 9/2005 | Zweig |
| 6,960,192 B1 | 11/2005 | Flaherty et al. |
| 7,001,360 B2 | 2/2006 | Veasey et al. |
| 7,048,715 B2 | 5/2006 | Diaz et al. |
| 7,060,059 B2 | 6/2006 | Keith et al. |
| 7,122,982 B2 | 10/2006 | Sasaya et al. |
| 7,128,727 B2 | 10/2006 | Flaherty et al. |
| 7,144,384 B2 | 12/2006 | Gorman et al. |
| 7,193,521 B2 | 3/2007 | Moberg et al. |
| D544,092 S | 6/2007 | Lewis |
| 7,247,149 B2 | 7/2007 | Beyerlein |
| 7,250,037 B2 | 7/2007 | Shermer et al. |
| 7,267,669 B2 | 9/2007 | Staunton et al. |
| 7,303,549 B2 | 12/2007 | Flaherty et al. |
| 7,390,314 B2 | 6/2008 | Stutz, Jr. et al. |
| 7,407,493 B2 | 8/2008 | Cane' |
| 7,455,663 B2 | 11/2008 | Bikovsky |
| 7,459,571 B2 | 12/2008 | Schlitter et al. |
| 7,465,290 B2 | 12/2008 | Reilly |
| 7,497,842 B2 | 3/2009 | Diaz et al. |
| 7,524,304 B2 | 4/2009 | Genosar |
| 7,530,964 B2 | 5/2009 | Lavi et al. |
| 7,547,281 B2 | 6/2009 | Hayes et al. |
| 7,563,253 B2 | 7/2009 | Tanner et al. |
| 7,565,208 B2 | 7/2009 | Harris et al. |
| 7,569,050 B2 | 8/2009 | Moberg et al. |
| D600,341 S | 9/2009 | Loerwald |
| 7,585,287 B2 | 9/2009 | Bresina et al. |
| 7,588,559 B2 | 9/2009 | Aravena et al. |
| D602,155 S | 10/2009 | Foley et al. |
| D602,586 S | 10/2009 | Foley et al. |
| D604,835 S | 11/2009 | Conley |
| 7,621,893 B2 | 11/2009 | Moberg et al. |
| 7,628,770 B2 | 12/2009 | Ethelfeld |
| 7,628,772 B2 | 12/2009 | McConnell et al. |
| 7,628,782 B2 | 12/2009 | Adair et al. |
| 7,637,891 B2 | 12/2009 | Wall |
| 7,641,649 B2 | 1/2010 | Moberg et al. |
| 7,660,627 B2 | 2/2010 | McNichols et al. |
| 7,678,079 B2 | 3/2010 | Shermer et al. |

(56) References Cited

U.S. PATENT DOCUMENTS

| | | |
|---|---|---|
| 7,682,338 B2 | 3/2010 | Griffin |
| 7,686,787 B2 | 3/2010 | Moberg et al. |
| 7,692,399 B2 | 4/2010 | Harriman et al. |
| 7,699,829 B2 | 4/2010 | Harris et al. |
| 7,699,833 B2 | 4/2010 | Moberg et al. |
| 7,704,227 B2 | 4/2010 | Moberg et al. |
| 7,704,231 B2 | 4/2010 | Pongpairochana et al. |
| 7,708,717 B2 | 5/2010 | Estes et al. |
| 7,713,238 B2 | 5/2010 | Mernoe |
| 7,713,240 B2 | 5/2010 | Istoc et al. |
| 7,717,913 B2 | 5/2010 | Novak et al. |
| 7,722,574 B2 | 5/2010 | Toman et al. |
| 7,736,344 B2 | 6/2010 | Moberg et al. |
| 7,744,589 B2 | 6/2010 | Mounce et al. |
| 7,749,194 B2 | 7/2010 | Edwards et al. |
| 7,753,879 B2 | 7/2010 | Mernoe |
| 7,766,873 B2 | 8/2010 | Moberg et al. |
| 7,776,030 B2 | 8/2010 | Estes et al. |
| 7,780,636 B2 | 8/2010 | Radmer et al. |
| 7,780,637 B2 | 8/2010 | Jerde et al. |
| 7,789,857 B2 | 9/2010 | Moberg et al. |
| 7,789,862 B2 | 9/2010 | Thorne, Jr. |
| 7,801,599 B2 | 9/2010 | Young et al. |
| 7,806,868 B2 | 10/2010 | De Polo et al. |
| 7,815,622 B2 | 10/2010 | Istoc et al. |
| 7,828,528 B2 | 11/2010 | Estes et al. |
| 7,837,659 B2 | 11/2010 | Bush, Jr. et al. |
| 7,846,132 B2 | 12/2010 | Gravesen et al. |
| 7,857,131 B2 | 12/2010 | Vedrine |
| 7,879,025 B2 | 2/2011 | Jacobson et al. |
| 7,879,026 B2 | 2/2011 | Estes et al. |
| 7,892,206 B2 | 2/2011 | Moberg et al. |
| 7,918,825 B2 | 4/2011 | O'Connor et al. |
| 7,918,843 B2 | 4/2011 | Genosar et al. |
| 7,935,104 B2 | 5/2011 | Yodfat et al. |
| 7,935,105 B2 | 5/2011 | Miller et al. |
| 7,938,803 B2 | 5/2011 | Mernoe et al. |
| 7,955,305 B2 | 6/2011 | Moberg et al. |
| 7,967,784 B2 | 6/2011 | Pongpairochana et al. |
| 7,981,105 B2 | 7/2011 | Adair et al. |
| 7,988,683 B2 | 8/2011 | Adair et al. |
| 7,993,300 B2 | 8/2011 | Nyholm et al. |
| 7,998,111 B2 | 8/2011 | Moberg et al. |
| 8,021,357 B2 | 9/2011 | Tanaka et al. |
| 8,025,658 B2 | 9/2011 | Chong et al. |
| 8,029,469 B2 | 10/2011 | Ethelfeld |
| 8,034,019 B2 | 10/2011 | Nair et al. |
| 8,038,666 B2 | 10/2011 | Triplett et al. |
| 8,057,436 B2 | 11/2011 | Causey et al. |
| 8,062,253 B2 | 11/2011 | Nielsen et al. |
| 8,062,257 B2 | 11/2011 | Moberg et al. |
| 8,065,096 B2 | 11/2011 | Moberg et al. |
| 8,066,694 B2 | 11/2011 | Wagener |
| D650,079 S | 12/2011 | Presta et al. |
| D652,503 S | 1/2012 | Cameron et al. |
| 8,105,279 B2 | 1/2012 | Mernoe et al. |
| 8,114,046 B2 | 2/2012 | Covino et al. |
| 8,114,064 B2 | 2/2012 | Alferness et al. |
| 8,114,066 B2 | 2/2012 | Naef et al. |
| 8,147,446 B2 | 4/2012 | Yodfat et al. |
| 8,152,764 B2 | 4/2012 | Istoc et al. |
| 8,152,770 B2 | 4/2012 | Reid |
| 8,152,779 B2 | 4/2012 | Cabiri |
| 8,152,793 B2 | 4/2012 | Keinanen et al. |
| 8,157,693 B2 | 4/2012 | Waksmundzki |
| 8,157,769 B2 | 4/2012 | Cabiri |
| 8,162,923 B2 | 4/2012 | Adams et al. |
| 8,167,841 B2 | 5/2012 | Teisen-Simony et al. |
| 8,172,804 B2 | 5/2012 | Bikovsky |
| 8,182,447 B2 | 5/2012 | Moberg et al. |
| 8,182,462 B2 | 5/2012 | Istoc et al. |
| 8,197,444 B1 | 6/2012 | Bazargan et al. |
| 8,206,351 B2 | 6/2012 | Sugimoto et al. |
| 8,267,893 B2 | 9/2012 | Moberg et al. |
| 8,267,921 B2 | 9/2012 | Yodfat et al. |
| 8,287,520 B2 | 10/2012 | Drew et al. |
| 8,308,679 B2 | 11/2012 | Hanson et al. |
| 8,348,898 B2 | 1/2013 | Cabiri |
| 8,372,039 B2 | 2/2013 | Mernoe et al. |
| 8,373,421 B2 | 2/2013 | Lindegger et al. |
| 8,409,142 B2 | 4/2013 | Causey et al. |
| 8,414,557 B2 | 4/2013 | Istoc et al. |
| 8,430,847 B2 | 4/2013 | Mernoe et al. |
| 8,469,942 B2 | 6/2013 | Kow et al. |
| 8,474,332 B2 | 7/2013 | Bente, IV et al. |
| 8,475,408 B2 | 7/2013 | Mernoe et al. |
| 8,479,595 B2 | 7/2013 | Vazquez et al. |
| 8,483,980 B2 | 7/2013 | Moberg et al. |
| 8,495,918 B2 | 7/2013 | Bazargan et al. |
| 8,512,287 B2 | 8/2013 | Cindrich et al. |
| 8,517,987 B2 | 8/2013 | Istoc et al. |
| 8,523,803 B1 | 9/2013 | Favreau |
| 8,556,856 B2 | 10/2013 | Bazargan et al. |
| 8,574,216 B2 | 11/2013 | Istoc et al. |
| 8,603,026 B2 | 12/2013 | Favreau |
| 8,603,027 B2 | 12/2013 | Favreau |
| 8,617,110 B2 | 12/2013 | Moberg et al. |
| 8,628,510 B2 | 1/2014 | Bazargan et al. |
| 8,647,074 B2 | 2/2014 | Moberg et al. |
| 8,647,296 B2 | 2/2014 | Moberg et al. |
| 8,668,672 B2 | 3/2014 | Moberg et al. |
| 8,674,288 B2 | 3/2014 | Hanson et al. |
| 8,679,060 B2 | 3/2014 | Mernoe et al. |
| 8,681,010 B2 | 3/2014 | Moberg et al. |
| 8,690,855 B2 | 4/2014 | Alderete, Jr. et al. |
| 8,708,961 B2 | 4/2014 | Field et al. |
| 8,751,237 B2 | 6/2014 | Kubota |
| 8,753,326 B2 | 6/2014 | Chong et al. |
| 8,753,331 B2 | 6/2014 | Murphy |
| 8,764,707 B2 | 7/2014 | Moberg et al. |
| 8,764,723 B2 | 7/2014 | Chong et al. |
| 8,771,222 B2 | 7/2014 | Kanderian, Jr. et al. |
| 8,777,896 B2 | 7/2014 | Starkweather et al. |
| 8,777,924 B2 | 7/2014 | Kanderian, Jr. et al. |
| 8,777,925 B2 | 7/2014 | Patton |
| 8,784,369 B2 | 7/2014 | Starkweather et al. |
| 8,784,370 B2 | 7/2014 | Lebel et al. |
| 8,790,295 B1 | 7/2014 | Sigg et al. |
| 8,795,224 B2 | 8/2014 | Starkweather et al. |
| 8,795,231 B2 | 8/2014 | Chong et al. |
| 8,795,260 B2 | 8/2014 | Drew |
| 8,801,668 B2 | 8/2014 | Ali et al. |
| 8,808,230 B2 | 8/2014 | Rotstein |
| 8,810,394 B2 | 8/2014 | Kalpin |
| 9,463,280 B2 | 10/2016 | Cabiri |
| 2001/0056263 A1 | 12/2001 | Alchas et al. |
| 2002/0040208 A1 | 4/2002 | Flaherty et al. |
| 2002/0043951 A1 | 4/2002 | Moberg |
| 2002/0055711 A1 | 5/2002 | Lavi et al. |
| 2003/0078195 A1 | 4/2003 | Kristensen et al. |
| 2003/0135159 A1 | 7/2003 | Daily et al. |
| 2003/0160683 A1 | 8/2003 | Blomquist |
| 2003/0171717 A1 | 9/2003 | Farrugia et al. |
| 2003/0199825 A1 | 10/2003 | Flaherty |
| 2004/0085215 A1 | 5/2004 | Moberg et al. |
| 2004/0092873 A1 | 5/2004 | Moberg |
| 2004/0116866 A1 | 6/2004 | Gorman et al. |
| 2004/0171983 A1 | 9/2004 | Sparks et al. |
| 2004/0260233 A1 | 12/2004 | Garibotto et al. |
| 2005/0065472 A1 | 3/2005 | Cindrich et al. |
| 2005/0070845 A1 | 3/2005 | Faries et al. |
| 2005/0071487 A1 | 3/2005 | Lu et al. |
| 2005/0171512 A1 | 8/2005 | Flaherty |
| 2005/0177136 A1 | 8/2005 | Miller |
| 2005/0197650 A1 | 9/2005 | Sugimoto et al. |
| 2005/0238507 A1 | 10/2005 | Dilanni et al. |
| 2005/0258714 A1 | 11/2005 | Henderson et al. |
| 2006/0095014 A1 | 5/2006 | Ethelfeld |
| 2006/0122577 A1 | 6/2006 | Poulsen et al. |
| 2006/0173408 A1 | 8/2006 | Wyrick |
| 2006/0173439 A1 | 8/2006 | Thorne et al. |
| 2006/0184154 A1 | 8/2006 | Moberg et al. |
| 2006/0229569 A1 | 10/2006 | Lavi et al. |
| 2006/0264890 A1 | 11/2006 | Moberg et al. |

(56) References Cited

U.S. PATENT DOCUMENTS

| | | |
|---|---|---|
| 2006/0283465 A1 | 12/2006 | Nickel et al. |
| 2007/0021733 A1 | 1/2007 | Hansen et al. |
| 2007/0049865 A1 | 3/2007 | Radmer et al. |
| 2007/0118405 A1 | 5/2007 | Campbell et al. |
| 2007/0149926 A1 | 6/2007 | Moberg et al. |
| 2007/0167912 A1 | 7/2007 | Causey et al. |
| 2007/0191770 A1 | 8/2007 | Moberg et al. |
| 2007/0219480 A1 | 9/2007 | Kamen et al. |
| 2007/0282269 A1 | 12/2007 | Carter et al. |
| 2008/0033369 A1 | 2/2008 | Kohlbrenner et al. |
| 2008/0051710 A1 | 2/2008 | Moberg et al. |
| 2008/0051711 A1 | 2/2008 | Mounce et al. |
| 2008/0051727 A1 | 2/2008 | Moberg et al. |
| 2008/0059133 A1 | 3/2008 | Edwards et al. |
| 2008/0125700 A1 | 5/2008 | Moberg et al. |
| 2008/0140006 A1 | 6/2008 | Eskuri et al. |
| 2008/0140018 A1 | 6/2008 | Enggaard et al. |
| 2008/0147004 A1 | 6/2008 | Mann et al. |
| 2008/0156476 A1 | 7/2008 | Smisson et al. |
| 2008/0167641 A1 | 7/2008 | Hansen et al. |
| 2008/0188813 A1 | 8/2008 | Miller et al. |
| 2008/0215006 A1 | 9/2008 | Thorkild |
| 2008/0221522 A1 | 9/2008 | Moberg et al. |
| 2008/0221523 A1 | 9/2008 | Moberg et al. |
| 2008/0269723 A1 | 10/2008 | Mastrototaro et al. |
| 2008/0294143 A1 | 11/2008 | Tanaka et al. |
| 2008/0306449 A1 | 12/2008 | Kristensen et al. |
| 2008/0312601 A1 | 12/2008 | Cane |
| 2008/0319416 A1 | 12/2008 | Yodfat et al. |
| 2009/0054750 A1 | 2/2009 | Jennewine |
| 2009/0076453 A1 | 3/2009 | Mejlhede et al. |
| 2009/0088694 A1 | 4/2009 | Carter et al. |
| 2009/0088731 A1 | 4/2009 | Campbell et al. |
| 2009/0093792 A1 | 4/2009 | Gross et al. |
| 2009/0093793 A1 | 4/2009 | Gross et al. |
| 2009/0124977 A1 | 5/2009 | Jensen |
| 2009/0149830 A1 | 6/2009 | Spector |
| 2009/0182277 A1 | 7/2009 | Carter |
| 2009/0234319 A1 | 9/2009 | Marksteiner |
| 2009/0240240 A1 | 9/2009 | Hines et al. |
| 2009/0253973 A1 | 10/2009 | Bashan et al. |
| 2009/0259176 A1 | 10/2009 | Yairi |
| 2009/0299397 A1 | 12/2009 | Ruan et al. |
| 2009/0326509 A1 | 12/2009 | Muse et al. |
| 2010/0030156 A1 | 2/2010 | Beebe et al. |
| 2010/0030198 A1 | 2/2010 | Beebe et al. |
| 2010/0037680 A1 | 2/2010 | Moberg et al. |
| 2010/0049144 A1 | 2/2010 | McConnell et al. |
| 2010/0057057 A1 | 3/2010 | Hayter et al. |
| 2010/0076412 A1 | 3/2010 | Rush et al. |
| 2010/0094255 A1 | 4/2010 | Nycz et al. |
| 2010/0100076 A1 | 4/2010 | Rush et al. |
| 2010/0100077 A1 | 4/2010 | Rush et al. |
| 2010/0106098 A1 | 4/2010 | Atterbury et al. |
| 2010/0121314 A1 | 5/2010 | Iobbi |
| 2010/0137790 A1 | 6/2010 | Yodfat |
| 2010/0145303 A1 | 6/2010 | Yodfat et al. |
| 2010/0162548 A1 | 7/2010 | Leidig |
| 2010/0168607 A1 | 7/2010 | Miesel |
| 2010/0168683 A1 | 7/2010 | Cabiri |
| 2010/0198157 A1 | 8/2010 | Gyrn et al. |
| 2010/0204657 A1 | 8/2010 | Yodfat et al. |
| 2010/0217192 A1 | 8/2010 | Moberg et al. |
| 2010/0217193 A1 | 8/2010 | Moberg et al. |
| 2010/0234830 A1 | 9/2010 | Straessler et al. |
| 2010/0241065 A1 | 9/2010 | Moberg et al. |
| 2010/0264931 A1 | 10/2010 | Lindegger et al. |
| 2010/0274112 A1 | 10/2010 | Hoss et al. |
| 2010/0274192 A1 | 10/2010 | Mernoe |
| 2010/0276411 A1 | 11/2010 | Hansen et al. |
| 2010/0280499 A1 | 11/2010 | Yodfat et al. |
| 2010/0331826 A1 | 12/2010 | Field et al. |
| 2011/0034900 A1 | 2/2011 | Yodfat et al. |
| 2011/0054399 A1 | 3/2011 | Chong et al. |
| 2011/0054400 A1 | 3/2011 | Chong et al. |
| 2011/0060284 A1 | 3/2011 | Harr |
| 2011/0119033 A1 | 5/2011 | Moberg et al. |
| 2011/0160654 A1 | 6/2011 | Hanson et al. |
| 2011/0160666 A1 | 6/2011 | Hanson et al. |
| 2011/0160669 A1 | 6/2011 | Gyrn et al. |
| 2011/0172645 A1 | 7/2011 | Moga et al. |
| 2011/0178472 A1 | 7/2011 | Cabiri |
| 2011/0184342 A1 | 7/2011 | Pesach et al. |
| 2011/0201998 A1 | 8/2011 | Pongpairochana et al. |
| 2011/0224614 A1 | 9/2011 | Moberg et al. |
| 2011/0233393 A1 | 9/2011 | Hanson et al. |
| 2011/0238031 A1 | 9/2011 | Adair et al. |
| 2011/0245773 A1 | 10/2011 | Estes et al. |
| 2011/0264383 A1 | 10/2011 | Moberg et al. |
| 2011/0270160 A1 | 11/2011 | Mernoe |
| 2011/0282282 A1 | 11/2011 | Lorenzen et al. |
| 2011/0295205 A1 | 12/2011 | Kaufmann et al. |
| 2011/0313238 A1 | 12/2011 | Reichenbach et al. |
| 2011/0313351 A1 | 12/2011 | Kamen et al. |
| 2011/0319861 A1 | 12/2011 | Wilk |
| 2011/0319919 A1 | 12/2011 | Curry et al. |
| 2012/0004602 A1 | 1/2012 | Hanson et al. |
| 2012/0004639 A1 | 1/2012 | Schoonmaker et al. |
| 2012/0010594 A1 | 1/2012 | Holt et al. |
| 2012/0022499 A1 | 1/2012 | Anderson et al. |
| 2012/0025995 A1 | 2/2012 | Moberg et al. |
| 2012/0029431 A1 | 2/2012 | Hwang et al. |
| 2012/0035546 A1 | 2/2012 | Cabiri |
| 2012/0041364 A1 | 2/2012 | Smith |
| 2012/0041370 A1 | 2/2012 | Moberg et al. |
| 2012/0041414 A1 | 2/2012 | Estes et al. |
| 2012/0071828 A1 | 3/2012 | Tojo et al. |
| 2012/0096953 A1 | 4/2012 | Bente, IV et al. |
| 2012/0096954 A1 | 4/2012 | Vazquez et al. |
| 2012/0101436 A1 | 4/2012 | Bazargan et al. |
| 2012/0108933 A1 | 5/2012 | Liang et al. |
| 2012/0160033 A1 | 6/2012 | Kow et al. |
| 2012/0165733 A1 | 6/2012 | Bazargan et al. |
| 2012/0165780 A1 | 6/2012 | Bazargan et al. |
| 2012/0215169 A1 | 8/2012 | Moberg et al. |
| 2012/0215199 A1 | 8/2012 | Moberg et al. |
| 2012/0226234 A1 | 9/2012 | Bazargan et al. |
| 2012/0259282 A1 | 10/2012 | Alderete, Jr. et al. |
| 2012/0296174 A1 | 11/2012 | McCombie et al. |
| 2012/0310153 A1 | 12/2012 | Moberg et al. |
| 2013/0060194 A1 | 3/2013 | Rotstein |
| 2013/0068319 A1 | 3/2013 | Plumptre et al. |
| 2013/0096509 A1 | 4/2013 | Avery et al. |
| 2013/0133438 A1 | 5/2013 | Kow et al. |
| 2013/0175192 A1 | 7/2013 | Iio et al. |
| 2013/0218089 A1 | 8/2013 | Davies et al. |
| 2013/0218092 A1 | 8/2013 | Davies et al. |
| 2013/0237953 A1 | 9/2013 | Kow et al. |
| 2013/0245595 A1 | 9/2013 | Kow et al. |
| 2013/0253419 A1 | 9/2013 | Favreau |
| 2013/0253420 A1 | 9/2013 | Favreau |
| 2013/0253421 A1 | 9/2013 | Favreau |
| 2013/0253472 A1 | 9/2013 | Cabiri |
| 2013/0331791 A1 | 12/2013 | Gross et al. |
| 2014/0055073 A1 | 2/2014 | Favreau |
| 2014/0055076 A1 | 2/2014 | Favreau |
| 2014/0058349 A1 | 2/2014 | Bazargan et al. |
| 2014/0083517 A1 | 3/2014 | Moia et al. |
| 2014/0094755 A1 | 4/2014 | Bazargan et al. |
| 2014/0128807 A1 | 5/2014 | Moberg et al. |
| 2014/0128835 A1 | 5/2014 | Moberg et al. |
| 2014/0135692 A1 | 5/2014 | Alderete, Jr. et al. |
| 2014/0135694 A1 | 5/2014 | Moberg et al. |
| 2014/0142499 A1 | 5/2014 | Moberg et al. |
| 2014/0148784 A1 | 5/2014 | Anderson et al. |
| 2014/0148785 A1 | 5/2014 | Moberg et al. |
| 2014/0163522 A1 | 6/2014 | Alderete, Jr. et al. |
| 2014/0163526 A1 | 6/2014 | Cabiri et al. |
| 2014/0171881 A1 | 6/2014 | Cabiri |
| 2014/0194819 A1 | 7/2014 | Maule et al. |
| 2014/0207064 A1 | 7/2014 | Yavorsky |
| 2014/0207065 A1 | 7/2014 | Yavorsky |
| 2014/0207066 A1 | 7/2014 | Yavorsky |
| 2014/0207080 A1 | 7/2014 | Allerdings |

(56) References Cited

U.S. PATENT DOCUMENTS

| | | | |
|---|---|---|---|
| 2014/0210631 | A1 | 7/2014 | Zavis |
| 2014/0213975 | A1 | 7/2014 | Clemente et al. |
| 2014/0236087 | A1 | 8/2014 | Alderete, Jr. et al. |
| 2014/0261758 | A1 | 9/2014 | Wlodarczyk et al. |
| 2014/0288511 | A1 | 9/2014 | Tan-Malecki et al. |
| 2014/0330240 | A1 | 11/2014 | Cabiri et al. |
| 2015/0011965 | A1 | 1/2015 | Cabiri |
| 2015/0011976 | A1 | 1/2015 | Vouillamoz et al. |
| 2015/0032084 | A1 | 1/2015 | Cabiri |
| 2015/0119797 | A1 | 4/2015 | Cabiri |
| 2015/0224253 | A1 | 8/2015 | Cabiri |
| 2016/0015910 | A1 | 1/2016 | Mukai et al. |
| 2017/0028132 | A1 | 2/2017 | Cronenberg et al. |

FOREIGN PATENT DOCUMENTS

| | | |
|---|---|---|
| CN | 102022308 A | 4/2011 |
| CN | 102083483 A | 6/2011 |
| EP | 0401179 | 12/1990 |
| EP | 0744975 A1 | 12/1996 |
| EP | 1666080 A1 | 6/2006 |
| EP | 2060606 A1 | 5/2009 |
| EP | 2345441 A1 | 7/2011 |
| EP | 2454483 B1 | 8/2015 |
| WO | 8911302 A1 | 11/1989 |
| WO | 9009202 A1 | 8/1990 |
| WO | 9521645 A1 | 8/1995 |
| WO | 9632975 A1 | 10/1996 |
| WO | 9721457 A1 | 6/1997 |
| WO | 9733638 A1 | 9/1997 |
| WO | 2007092618 A2 | 8/2007 |
| WO | 2007130868 A1 | 11/2007 |
| WO | 2008024810 A2 | 2/2008 |
| WO | 2008024814 A2 | 2/2008 |
| WO | 2008129549 A1 | 10/2008 |
| WO | 2009081262 A1 | 7/2009 |
| WO | 2011090955 A1 | 7/2011 |
| WO | 2011113806 A1 | 9/2011 |
| WO | 2012032411 A2 | 3/2012 |
| WO | 2013115843 A1 | 8/2013 |
| WO | 2013148270 A2 | 10/2013 |
| WO | 2013173092 A1 | 11/2013 |
| WO | 2014081411 A1 | 5/2014 |
| WO | 2014179210 A1 | 11/2014 |

OTHER PUBLICATIONS

U.S. Appl. No. 13/886,867 by Cabiri, filed May 3, 2013.
Int'l Search Report and Written Opinion dated Apr. 5, 2013 in Int'l Application No. PCT/US2012/050696.
Office Action dated Aug. 15, 2013 in U.S. Appl. No. 13/429,942 by Cabiri.
Office Action dated Jan. 16, 2014 in U.S. Appl. No. 13/429,942 by Cabiri.
Int'l Search Report and Written Opinion dated Jun. 30, 2014 in Int'l Application No. PCT/US2013/031598.
Int'l Search Report and Written Opinion dated Aug. 28, 2014 in Int'l Application No. PCT/US2014/035662.
Int'l Preliminary Report on Patentability dated Aug. 14, 2014 in Int'l Application No. PCT/US2012/050696.
U.S. Appl. No. 14/372,384 by Cabiri, filed Jul. 15, 2014.
Office Action dated Jan. 28, 2015 in U.S. Appl. No. 13/429,942 by Cabiri.
U.S. Appl. No. 14/593,041 by Cabiri, filed Jan. 9, 2015.
U.S. Appl. No. 14/683,253 by Cabiri, filed Apr. 10, 2015.
Office Action dated May 18, 2015 in U.S. Appl. No. 13/429,942 by Cabiri.
Office Action dated Nov. 25, 2015 in U.S. Appl. No. 14/372,384 by Cabiri.
Office Action dated Oct. 28, 2015 in U.S. Appl. No. 13/429,942 by Cabiri.
Office Action dated Jan. 5, 2016 in U.S. Appl. No. 14/696,644 by Cabiri.
Office Action dated Dec. 3, 2015 in CN Application No. 201280068544.0.
Office Action dated Feb. 24, 2016 in U.S. Appl. No. 13/429,942 by Cabiri.
Int'l Preliminary Report on Patentability dated Oct. 9, 2014 in Int'l Application No. PCT/US13/31598.
Int'l Preliminary Report on Patentability dated Nov. 12, 2015 in Int'l Application No. PCT/US14/35662.
Office Action dated Apr. 19, 2016 in U.S. Appl. No. 14/372,384 by Cabiri.
Office Action dated May 17, 2016 in U.S. Appl. No. 13/886,867 by Cabiri.
Office Action dated Jun. 1, 2016 in CN Application No. 2013800274556.
Office Action dated Jun. 17, 2016 in CN Application No. 201280068544.0.
Office Action dated Jul. 29, 2016 in U.S. Appl. No. 14/696,644, by Cabiri.
Office Action dated Sep. 30, 2016 in U.S. Appl. No. 13/886,867, by Cabiri.
Office Action dated Nov. 9, 2016 in U.S. Appl. No. 14/683,253, by Cabiri.
Office Action dated Mar. 7, 2017 in U.S. Appl. No. 14/696,644, by Cabiri.
Office Action dated Mar. 13, 2017 in U.S. Appl. No. 14/372,384, by Cabiri.
Office Action dated Feb. 15, 2017 in CN Application No. 2013800274556.
Office Action dated Jan. 17, 2017 in EP Application No. 13716886.
Office Action dated Apr. 20, 2017 in U.S. Appl. No. 13/886,867, by Cabiri.
Examination Report dated May 8, 2017 in EP Application No. 12750951.1.
Office Action dated Aug. 10, 2017 in U.S. Appl. No. 14/372,384, by Cabiri.
Office Action dated Sep. 8, 2017 is U.S. Appl. No. 15/510,846, by Aida.
Office Action dated Nov. 17, 2017 in U.S. Appl. No. 14/510,846, by Cabiri.
Office Action dated Nov. 14, 2017 in U.S. Appl. No. 14/593,041, by Cabiri.

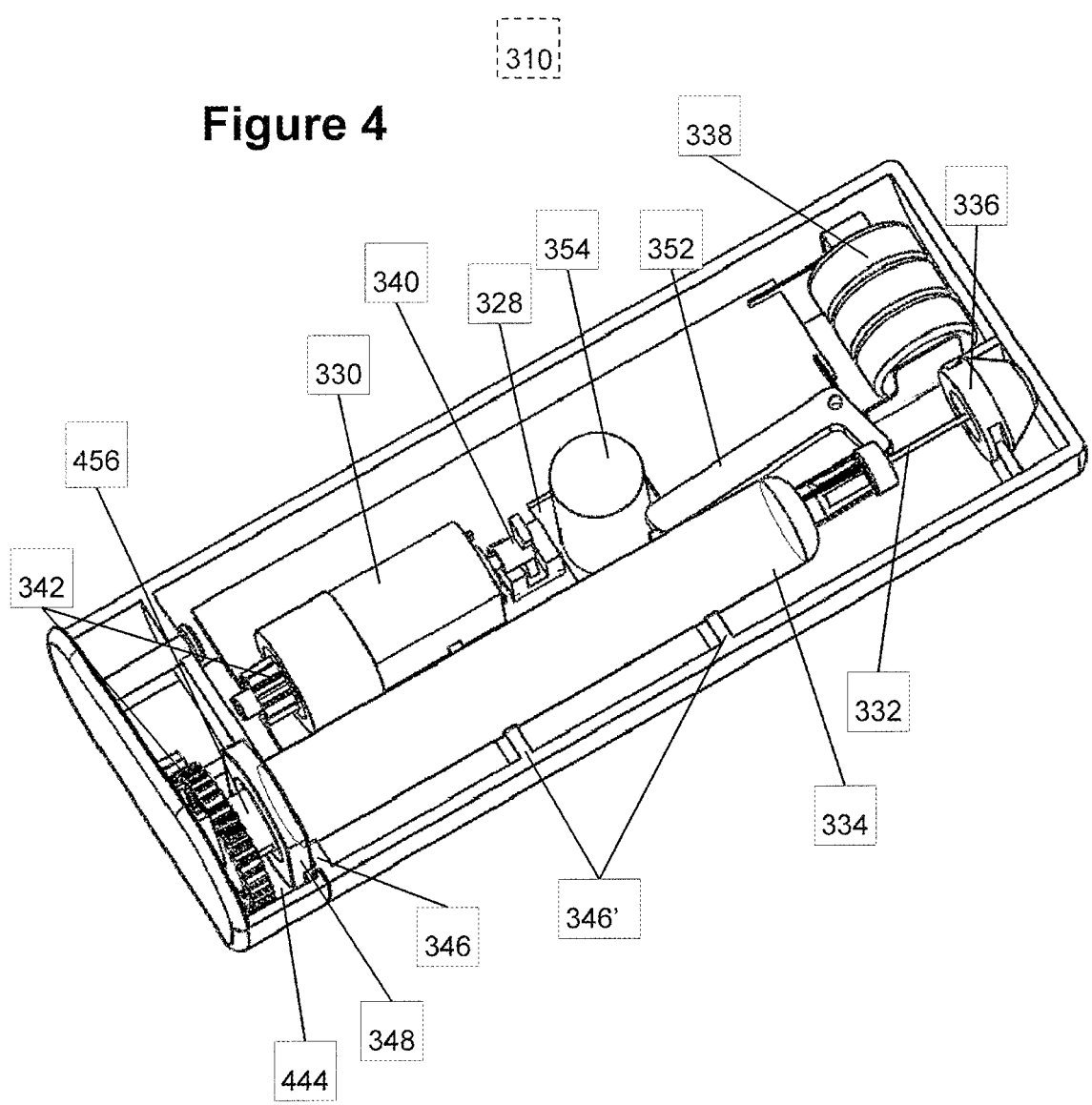

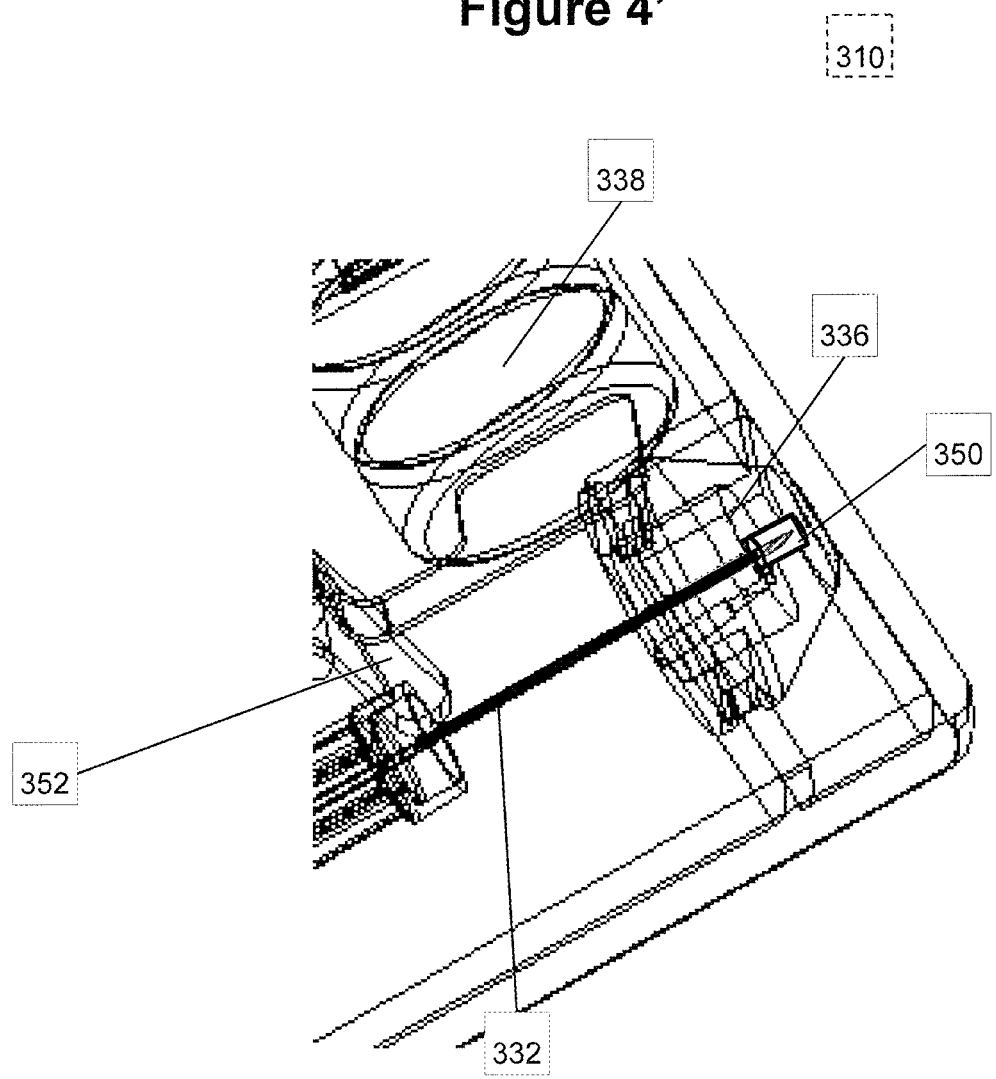

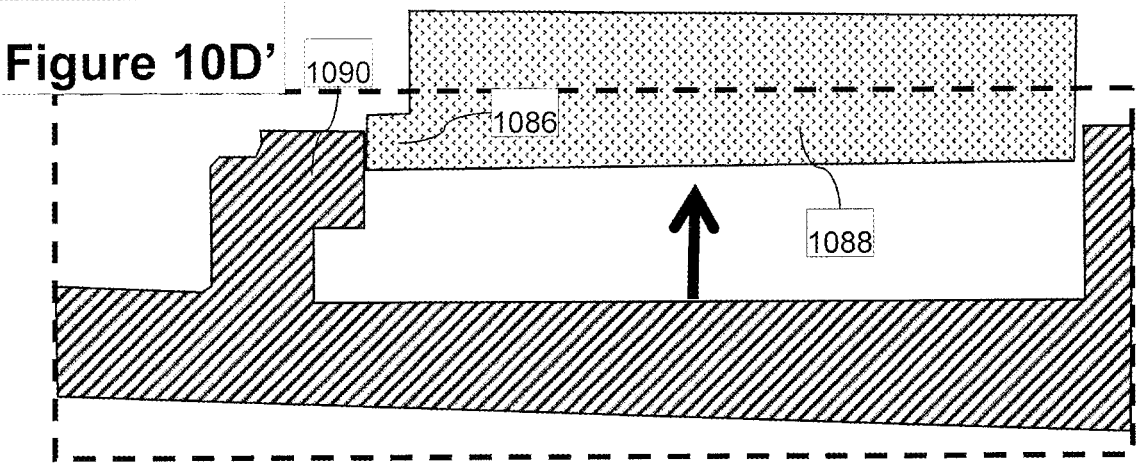
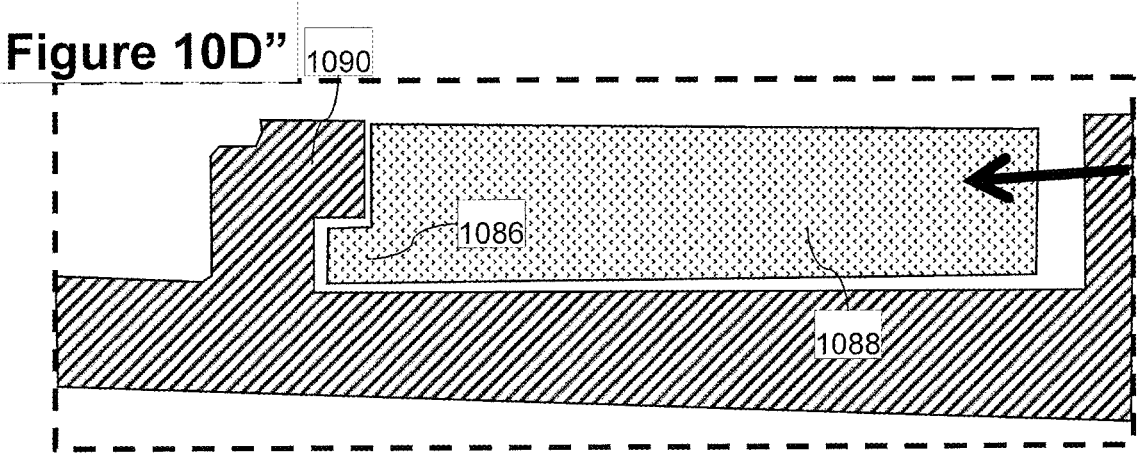

MOTION ACTIVATED MECHANISMS FOR A DRUG DELIVERY DEVICE

CROSS-REFERENCE TO RELATED APPLICATIONS

This application is a Section 371 of International Application No. PCT/US13/31598, filed on Mar. 14, 2013, which is a Continuation-in-Part of U.S. application Ser. No. 13/429,942, filed on Mar. 26, 2012, now U.S. Pat. No. 9,463,280, issued on Oct. 11, 2016, the disclosure of each of which is incorporated by reference herein in its entirety.

FIELD AND BACKGROUND OF THE INVENTION

The present invention, in some embodiments thereof, relates to an apparatus wearable by a recipient and method for delivering a substance to a recipient, more particularly, but not exclusively, to an apparatus with a mechanical drive train for priming the apparatus, for example by unsealing a reservoir containing a drug and/or by locking a door and subsequently delivering the drug to a recipient.

US published patent application 2009/0093792 to the present author discloses an apparatus for administering a substance to a subject. A vial contains the substance and a stopper is disposed within the vial and is slidably coupled to the vial. A first threaded element is (a) rotatable with respect to the vial and (b) substantially immobile proximally with respect to the vial during rotation of the first threaded element. A second threaded element is threadably coupled to the first threaded element. At least a distal end of the second threaded element is substantially non-rotatable with respect to the vial, and the distal end of the second threaded element defines a coupling portion that couples the second threaded element to the stopper. The first threaded element, by rotating, linearly advances the stopper and at least the distal end of the second threaded element toward a distal end of the vial. A vial piercing mechanism is movably (e.g., rotatably) coupled to a housing base. As part of the insertion of vial into the housing base, a seal at distal end of the vial is pierced by pressing the seal against the piercing mechanism. The substance is configured to subsequently flow through a tube toward an activation mechanism, which is typically coupled to the housing base, and is configured to insert a cannula and/or a needle through the subject's skin and to deliver the substance via the cannula and/or the needle.

U.S. Pat. No. 5,858,001 to Tsals discloses a liquid drug delivery device adapted to be adhered to the skin of a subject by a base member defining a skin-contacting surface having an adhesive coating. A columnar cartridge serves as reservoir for the drug and is incorporated in a housing, which is connected to the base member such that in use the longitudinal axis of the cartridge is disposed substantially parallel to the skin-contacting surface. A delivery needle communicating in use with the interior of the cartridge penetrates the skin of the subject when the housing snaps downward relative to the base member. This action also causes the actuation of a citric acid/sodium bicarbonate gas generator which generates a gas to move a piston within the cartridge, compressing the drug compartment. This compression causes a stopper to be penetrated by a conduit in communication with the delivery needle, allowing the drug to be ejected from the compartment through the needle and into the subcutaneous tissue of the subject.

US published patent application 2006/0173408 to Wyrick discloses a reloadable medicine injector and methods in which a barrel with a receiving cavity is adapted to slidably to receive a syringe subassembly for axial movement therein. Upon removal of a safety and release of a syringe driver, the syringe driver moves forward and injects the syringe needle. A plurality of penetration controls are shown for controlling injection needle penetration depth. In some embodiments, the injector makes use of a double needle assembly in which a double needle hub mounts a seal penetration needle that projects rearwardly toward a penetrable seal on the associated ampule. A flesh penetration needle projects forwardly. In practice, both needles can be made integral.

U.S. Pat. No. 5,997,501 to Gross discloses an intradermal drug delivery device comprising a housing having a drug reservoir therewithin. A microprocessor-controlled electrolytic cell provides gas to expand a gas generation chamber and thereby contract the reservoir. A hollow needle, communicating at an inner end thereof with the reservoir, extends from a lower surface of the housing such that contraction of the reservoir forces drug to escape therefrom via the needle. The device permits delivery of drugs of relatively large molecular weights at slow rates.

US published patent application 2011/0178472 and PCT application WO 2011/090955 to the present author disclose a needle assembly adapted for fluid communication with a cartridge containing a substance to be delivered to a subject. The needle assembly characterized by a biasing device arranged to apply a biasing force on a needle to cause the needle to protrude outwards of a housing to pierce the subject, and biasing device release apparatus including a biasing device arrestor that initially blocks movement of the biasing device. After finishing the drug administration, the needle release apparatus lifted off the patient's body, which causes the safety latch to move back to the down position and the needle to be retracted back into the housing.

A safety latch position sensor is provided for sensing when safety latch moves to an up position indicating that the device has been attached to a patient. A controller initiates operation of an actuator after a predetermined time delay (e.g., 5-15 seconds) to ensure that the drug delivery apparatus was indeed placed on purpose on the patient for delivering the drug. When operated, the actuator rotates a shaft causing the biasing device arrestor to move linearly out of an aperture. As soon as the biasing device arrestor has moved out of the aperture, the biasing device is no longer blocked and it now pushes down on a needle piercing the patient's skin.

Additional background art includes US published patent applications 2011/0178472 to the same author, U.S. Pat. No. 7,789,862 to Thorne, U.S. Pat. No. 7,780,636 to Radmer, U.S. Pat. No. 5,957,895 to Sage, U.S. Pat. No. 7,918,843 to Genosar, and U.S. Pat. No. 7,789,862 to Thorne.

SUMMARY OF THE INVENTION

According to an aspect of some embodiments of the present invention there is provided an apparatus wearable by a recipient having a single motion drive train for sequentially unsealing a reservoir and delivering a drug to the recipient. The apparatus may include a seal of the reservoir. The apparatus may also include a controlled rate power source. The apparatus may also include a plunger driven by the controlled rate power source. The apparatus may also include a hollow needle. An initial movement of the plunger may drive the hollow needle through the seal and subsequent movement of the plunger may discharge the drug from the reservoir.

According to some embodiments of the invention, the controlled rate power source may include a direct current motor, a stepper motor and/or a linear actuator.

According to some embodiments of the invention, the apparatus may further include a surface configured for attaching to a skin of the recipient.

According to some embodiments of the invention, the apparatus may further include a pathway for movement of the reservoir. The initial movement of the plunger may impel the reservoir along the pathway.

According to some embodiments of the invention, the pathway may be substantially parallel to the surface.

According to some embodiments of the invention, the plunger may be configured for discharging a liquid having a viscosity of at least 10 centipoise.

According to some embodiments of the invention, the plunger may be configured for discharging at a substantially constant rate for at least 1 minute.

According to some embodiments of the invention, the reservoir may be configured for long term storage of the drug inside of the apparatus.

According to some embodiments of the invention, the apparatus may further include a hypodermic needle and a needle release for inserting the hypodermic needle into the recipient. The needle release may be synchronized to the plunger.

According to some embodiments of the invention, a direction of the needle release may be non-parallel to a direction of the movement of the plunger.

According to some embodiments of the invention, a direction of the needle release may be substantially orthogonal to a direction of the movement of the plunger.

According to some embodiments of the invention, the apparatus may further include a processor for controlling the controlled rate power source.

According to some embodiments of the invention, the apparatus may further include a septum located in a needle opening of the apparatus. Upon release of a hypodermic needle, the hypodermic needle may puncture the septum before being inserted into the recipient.

According to some embodiments of the invention, the apparatus may further include a rotation sensor. The controlling may be according to an output of the rotation sensor.

According to some embodiments of the invention, the apparatus may further include a rotation sensor. The processor may sense the puncturing of the seal based on an output of the rotation sensor.

According to some embodiments of the invention, the hollow needle may be initially in fluid communication with the reservoir. The seal may be configured for sealing the hollow needle.

According to some embodiments of the invention, the reservoir may include a cartridge insertable into the apparatus.

According to an aspect of some embodiments of the present invention there is provided a method for delivering a drug to a recipient with a delivery apparatus. The drug may be contained in a reservoir initially sealed by a seal for long term aseptic storage. The delivery apparatus may include a hollow needle and a plunger. The method may include attaching a surface of the delivery apparatus to the recipient. The method may also include applying a force with the plunger to contents of the reservoir. The method may also include puncturing the seal with the hollow needle by the force. The method may also include discharging the drug from the reservoir by the force subsequent to the puncturing. The method may also include detecting a rate of the discharging, and the method may also include adjusting the rate of the discharging based on a result of the detecting.

According to some embodiments of the invention, the applying of the force may be in a direction substantially parallel to the surface.

According to some embodiments of the invention, the method may further include supplying a torque, and converting the torque into the force.

According to some embodiments of the invention, the detecting may be by measuring a rotation driven by the torque.

According to some embodiments of the invention, the discharging may be at a substantially constant rate for at least 1 minute.

According to some embodiments of the invention, the method may further include releasing a hypodermic needle into the recipient by the apparatus subsequent to the puncturing.

According to some embodiments of the invention, the method may further include releasing a hypodermic needle by the apparatus into the recipient in a direction non-parallel to the applying of the force.

According to some embodiments of the invention, the method may further include releasing a hypodermic needle by the apparatus into the recipient in a direction substantially orthogonal to the applying of the force.

According to some embodiments of the invention, the method may further include sensing by the delivery apparatus of a puncturing of the seal.

According to an aspect of some embodiments of the present invention, there is provided a method for delivering a drug to a recipient with a delivery apparatus, the apparatus may include an internal space initially sealed by a septum for long term aseptic storage. The delivery apparatus may also include a needle and a processor. The method may include attaching a surface of the delivery apparatus to the recipient. The method may also include puncturing the septum with the needle in response to a command of the processor. The method may also include discharging the drug subsequent to puncturing the septum. The method may also include, detecting a rate of the discharging and adjusting by the processor of the rate of the discharging based on a result of the detecting.

According to some embodiments of the invention, the discharging may be driven by an actuator.

According to some embodiments of the invention, the puncturing may be triggered by the actuator.

According to some embodiments of the invention, the actuator may include a motor. The method may further include transforming a rotational motion of the motor into a linear motion. The discharging may be driven by the linear motion.

According to some embodiments of the invention, the septum may seal a needle opening in a housing of the apparatus.

According to some embodiments of the invention, the needle may include a hypodermic needle. The method may further include inserting the hypodermic needle into the recipient subsequent to the puncturing and prior to the discharging.

According to an aspect of some embodiments of the present invention, there is provided an apparatus wearable by a recipient for delivering a drug to the recipient. The apparatus may include an initially aseptic internal space. The apparatus may also include a septum initially sealing the internal space. The apparatus may also include a controlled rate power source. The apparatus may also include a plunger driven by the controlled rate power source, and a hollow needle. The controlled rate power source may trigger puncturing the septum by the hollow needle, and subsequently, the power source may drive movement of the plunger, discharging the drug from the reservoir.

According to an aspect of some embodiments of the present invention there is provided a method for delivering a drug to a recipient with a drug delivery device. The drug delivery device may include an attaching base and a mechanical drive train and a reservoir containing the drug. The method may include attaching the base to the recipient; driving a mechanical element with a motion of the mechanical drive train to prime the delivery device while attached to the recipient, and subsequently impelling a plunger into the reservoir by continued motion of the drive train, the plunger discharging the drug from the reservoir.

According to some embodiments of the invention, the priming is irreversible. According to some embodiments of the invention, the priming includes unsealing the reservoir. According to some embodiments of the invention, the unsealing includes puncturing a septum with a hollow needle and the discharging is through the hollow needle.

According to some embodiments of the invention, the priming includes locking a door closed at least partially blocking an opening for accessing the reservoir. According to some embodiments of the invention, the reservoir is contained in a cartridge and the method may further include inserting the cartridge through the opening into the apparatus prior to the locking.

According to some embodiments of the invention, the method may further include sensing a rate of the discharging and adjusting the motion according to a result of the sensing. According to some embodiments of the invention, the motion is substantially parallel to the base. According to some embodiments of the invention, the discharging is at a substantially constant rate for at least 1 minute.

According to some embodiments of the invention, the method may further include inserting a hypodermic needle into the recipient.

According to some embodiments of the invention, a direction of the needle release is non-parallel to the path of motion.

According to some embodiments of the invention, the releasing is in a direction substantially orthogonal to the path of motion.

According to some embodiments of the invention, the method may further include rotating a gear and the rotating may power the motion.

According to an aspect of some embodiments of the present invention there is provided an apparatus for delivering a drug to a recipient. The apparatus may include an attaching base for attachment to the recipient; a mechanical drive train; a reservoir containing the drug; a priming mechanism driven by the motion, and a plunger configured to be impelled into the reservoir by the drive train subsequent to the priming thereby discharging the drug from the reservoir.

According to some embodiments of the invention, the priming is irreversible.

According to some embodiments of the invention, the apparatus may further include a seal initially sealing the reservoir preventing the discharging and a puncturing mechanism configured for being driven through the seal by an initial movement of the drive train.

According to some embodiments of the invention, the puncturing mechanism includes a hollow needle and the discharging is through the hollow needle.

According to some embodiments of the invention, the apparatus may further include an opening for accessing the reservoir; a door having a closed position at least partially blocking the opening, and a locking mechanism driven by the motion to lock the door in the closed position.

According to some embodiments of the invention, the reservoir is included in a cartridge and the cartridge is configured for insertion through the opening into the apparatus.

According to some embodiments of the invention, the apparatus may further include a controlled rate power source driving the drive train.

According to some embodiments of the invention, the controlled rate power source includes at least one element selected from the group consisting of a direct current motor, a stepper motor, and a linear actuator.

According to some embodiments of the invention, the motion is substantially parallel to the base.

According to some embodiments of the invention, the plunger is configured for discharging a liquid having a viscosity of at least 10 centipoise.

According to some embodiments of the invention, plunger is configured for discharging at a substantially constant rate for at least 1 minute.

According to some embodiments of the invention, reservoir is configured for long term storage of the drug inside of the apparatus.

According to some embodiments of the invention, the apparatus may further include a hypodermic needle, and a needle release for inserting the hypodermic needle into the recipient.

According to some embodiments of the invention, the needle release is activated by the motion.

According to some embodiments of the invention, a direction of the needle release is non-parallel path of motion.

According to some embodiments of the invention, a direction of the needle release is substantially orthogonal path of motion.

According to some embodiments of the invention, the apparatus may further include a temporary latch, the temporary latch holding the door in a closed position prior to the locking.

According to some embodiments of the invention, the locking is irreversible.

According to some embodiments of the invention, the locking occurs after a time delay.

According to some embodiments of the invention, the apparatus may further include a septum located in a needle opening of the apparatus such that upon release the hypodermic needle punctures the septum before being inserted into the recipient.

According to some embodiments of the invention, the apparatus may further include a processor for controlling the controlled rate power source.

According to some embodiments of the invention, the apparatus may further include an injection rate sensor and wherein the controlling is according to an output of the injection rate sensor.

According to some embodiments of the invention, the processor is configured for further sensing progress of at least one action selected from the group of the priming and the discharging.

According to some embodiments of the invention, the injection rate sensor includes a rotation sensor.

According to some embodiments of the invention, the hollow needle is initially in fluid communication with the reservoir, and the seal is configured for sealing the hollow needle.

According to some embodiments of the invention, the apparatus may further include a cartridge insertable into the apparatus, the reservoir being included in the cartridge.

According to some embodiments of the invention, the apparatus may further include a lock activated by the drive train.

According to some embodiments of the invention, the base may include an adhesive for the attachment.

According to some embodiments of the invention, the lock includes at least one element selected from the group consisting of a bolt and a pressure activated latch.

According to some embodiments of the invention, the door has a slack and the driving of the locking mechanism includes restraining the slack.

According to an aspect of some embodiments of the present invention there is provided a method for delivering a drug to a recipient with a delivery apparatus, the drug contained in a reservoir initially sealed by a seal for long term aseptic storage, the delivery apparatus including a hollow needle and a plunger. The method may include impelling the plunger into the reservoir via motion of a mechanical drive train; puncturing the seal by driving the hollow needle through the seal via the motion; discharging the drug from the reservoir by via the motion subsequent to the puncturing; detecting a rate of the discharging, and adjusting a rate of the motion based on a result of the detecting.

According to some embodiments of the invention, the method may further include attaching the delivery apparatus to the recipient.

According to some embodiments of the invention, the method may further include delivering the drug into the recipient at an injection site. The motion may be in a direction substantially parallel to a skin surface of the recipient at the injection site.

According to some embodiments of the invention, the method may further include supplying a rotating actuator and converting the rotating into the motion.

According to some embodiments of the invention, the detecting is by measuring the rotation.

According to some embodiments of the invention, the discharging is at a substantially constant rate for at least 1 minute.

According to some embodiments of the invention, the method may further include releasing a hypodermic needle by the delivery apparatus into the recipient subsequent to the puncturing.

According to some embodiments of the invention, the method may further include releasing a hypodermic needle by the delivery apparatus into the recipient in a direction non-parallel to the motion.

According to some embodiments of the invention, the method may further include releasing a hypodermic needle by the delivery apparatus into the recipient in a direction substantially orthogonal to the motion.

According to some embodiments of the invention, the method may further include sensing by the delivery apparatus of the puncturing.

According to some embodiments of the invention, the method may further include activating a locking mechanism of the apparatus by means of the motion.

According to an aspect of some embodiments of the present invention there is provided a method for delivering a drug to a recipient with a delivery apparatus. The delivery apparatus may include an internal space initially sealed by a septum for long term aseptic storage, a needle and a processor. The method may include puncturing the septum with the needle in response to a command of the processor; discharging the drug subsequent to the puncturing; detecting a rate of the discharging, and adjusting by the processor the rate of the discharging based on a result of the detecting.

According to some embodiments of the invention, the discharging is driven by an actuator.

According to some embodiments of the invention, the puncturing is triggered by the actuator.

According to some embodiments of the invention, actuator may further include a motor and the method may further include transforming a rotational motion of the motor into a translational motion, and the discharging may be driven by the translational motion.

According to some embodiments of the invention, the septum seals a needle opening in a housing of the delivery apparatus.

According to some embodiments of the invention, the needle may include a hypodermic needle, and the method may further include inserting the needle into the recipient subsequent to the puncturing and prior to the discharging.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 3' is a close perspective view of the septum of the embodiment of FIG. 3 prior to puncturing the septum;

FIG. 4 is a perspective view of the mechanism the embodiment of FIG. 3 after puncturing the septum;

FIG. 4' is a close perspective view of the septum of the embodiment of FIG. 3 after puncturing the septum;

DESCRIPTION OF SPECIFIC EMBODIMENTS OF THE INVENTION

Overview

Figure 1:
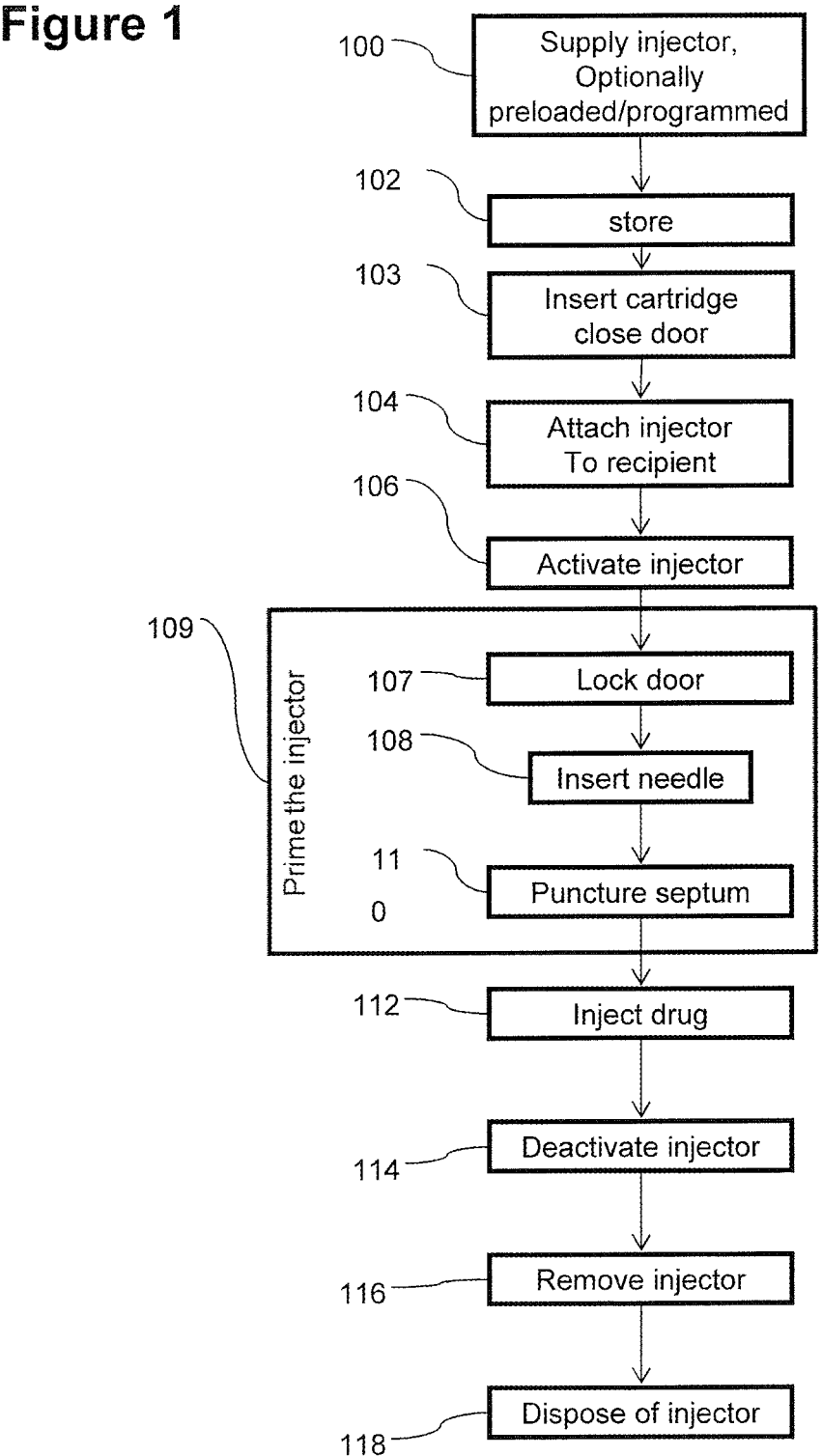
FIG. 1 is a flow chart illustrating an exemplary embodiment of a method for unsealing a reservoir and delivering a drug.

The present invention, in some embodiments thereof, relates to an apparatus wearable by a recipient and method for delivering a substance to a recipient, more particularly, but not exclusively, to an apparatus with a mechanical drive train for priming the apparatus, for example by unsealing a reservoir containing a drug and/or by locking a door and subsequently delivering the drug to a recipient.

Drive One Motion and/or Parallel to Base/Small Light

In some embodiments, an unsealing mechanism and/or a locking mechanism may use the existing drive train of the drug discharge device. For example, the drive train may include a controlled rate power source for example a motor driving a mechanical drive train. For example, the drive train may include a screw assembly that transforms the revolving motion of the motor into a linear motion. For example, the drive train may include a telescoping assembly. In some embodiments, drive train may be unidirectional and/or irreversible, for example, a telescoping assembly may be designed to expand, but not to retract.

In some embodiments, the drive train may drive a series of mechanisms. The mechanisms may optionally be coupled to the drive in series without sliding or and/or without disengaging. For example, a mechanism may be driven until a stop and then further movement may push the next mechanism in series. For example, the drive train may optionally impel a plunger. Optionally, while the reservoir is sealed, the plunger may drive the reservoir along a direction of motion of the drive train toward an unsealing mechanism. The reservoir may, for example, collide with the unsealing mechanism and be unsealed. After unsealing, the reservoir optionally reaches a stop and ceases moving. Optionally after unsealing the reservoir, further motion of the plunger may drive discharging of the drug.

In some embodiments, one or more mechanisms may be including in the path of the drive train. Optionally, motion of the drive train may activate one or all of the mechanism in its path. In some embodiments, the mechanisms may be activated sequentially and/or simultaneously. Optionally, a first mechanism may be activated until a stopping point at which point further motion of the drive train may activate a second mechanism. For example, a locking mechanism may be located in the path of the drive train. Optionally, while the door is unlocked, a part of the drive train and/or of the plunger and/or of the reservoir may be driven into a locking mechanism, thereby locking a door. For example, after locking the door, subsequent motion of the plunger may drive discharging of the drug. Optionally, motion of the drive train may activate release of a hypodermic needle. Optionally the needle may be released in a direction non-parallel to the motion. For example, the direction of needle release may range between 10° and 90° to the motion. The direction of release of the needle may optionally be substantially parallel to the motion. Optionally, motion of the drive may discharge a flushing fluid before and/or after the medicine.

In some embodiments, the drive train may induce linear movement. For example, a drive train may impel a plunger, which may optionally cause discharging of the drug. Optionally, the linear movement may additionally or alternatively drive a door locking mechanism. For example, the linear movement may cause additionally or alternatively unsealing of a reservoir. For example, the reservoir may be initially sealed with a septum. For example, while a reservoir is sealed, motion of the drive may drive a needle through the septum, unsealing the reservoir. Subsequently to unsealing the reservoir, motion of the drive may cause discharging of the medicine.

For example, the door may be locked when a drive train of the injector contacts a locking mechanism. For example, the drive train may expand, filling a space between a door locking mechanism and a plunger. The drive train may optionally expand backwards towards the locking mechanism. The drive train may eventually contact for example, the locking mechanism causing it to lock. Subsequently, the locking mechanism may, optionally, prevent further backwards motion of the drive train. Further expansion of the drive train may then push the plunger forward into the reservoir.

Optionally, there may be a time delay between activation of the infuser and priming of the infuser. For example, in some embodiments the time delay may range between five seconds and two minutes. For example, the time delay may be the time necessary for a telescoping assembly to fill and empty space. In some embodiments, the length of the empty space may for example be less than 3 mm. In some embodiments, the drive train may impart of force ranging for example between 1.0 and 4.0 kg. The length of movement of the drive for priming the pump may range, for example, between 0.4 and 8 mm. In some embodiments, a door lock door may resist an opening force of between 2-8 kg In some embodiments, the apparatus may be worn by the recipient. Wearing the apparatus may include, for example, attaching a base of the apparatus to the recipient and/or carrying the apparatus attached to clothing of the recipient and/or strapping the apparatus to the recipient. For example, the base of the apparatus may stick to the skin of the recipient (for example via an adhesive).

In some embodiments, there may be a time delay. For example, there may be time delay between activation of an infuser and the activation of a first mechanism. Alternatively or additionally, there may be a time delay between activation and/or stopping of one mechanism and activation of a second mechanism.

In some embodiments, the motion of the drive train may be substantially parallel to the base of the apparatus. For example, the path of motion of the drive train may make an angle between −10° to 10° with an attaching surface of the base.

Controlled Rate Deliver

In some embodiments, the rate of delivery may be controlled. Optionally a drug may be discharged as a bolus injection and/or continuously and/or at a slow rate and/or at a fast rate. Optionally the rate of discharge may be adjustable. Optionally a sensor may be used to indicate progress of an infusion process. For example, a sensor may measure motion of the drive train. Optionally, processor may user sensor measurement to indicate and/or adjust progress of discharge. For example, based on the rate of motion of the drive train, the processor may compute a rate of drug discharge. For example based on the motion of the drive train the processor may estimate whether a septum has been punctured and/or whether a door has been locked. For example, the rate of motion of the drive train may be adjusted according to results of the measurements.

In some embodiments, the maximum rate of delivery may optionally be between 10 ml/hr and 100 ml/hr. Optionally, the total delivered volume may be between 0.5 ml and 20 ml. In some embodiments, the total time of delivery may be between 5 seconds and 20 minutes. Optionally, the total time of delivery may be measured from the beginning of delivery until the end of delivery. Optionally, the beginning of deliver may be measured from the time of activation of the apparatus and/or alternatively from the time of attachment of the apparatus and/or alternatively from the time that delivery of the substance begins. Optionally the end of delivery may be measured at deactivation of the apparatus and/or alternatively at the earliest time after which no more of the substance is delivered and/or alternatively when the apparatus is removed from the recipient. Optionally the drug may be delivered in a single dose and/or at a constant rate.

Programmable

In some embodiments, a drug pump may be a programmable device. For example, the pump may be capable of controlled delivery of a substance according a preprogrammed schedule and/or rate. Alternatively or additionally, the pump may be a smart device capable of changing a delivery schedule according to commands and/or in reaction to changing conditions. Optionally, the device may be capable of stopping and restarting delivery.

Sealed for Long Term Storage and Ready to Use

A drug may require strictly prescribed packaging. Legal, health and safety requirements may include very stringent packaging standards. Packages may need to be aseptic, packaging materials may be strictly limited and package geometry may be very precisely stipulated. For example, when a drug is to be stored for a significant period of time (for example more than 24 hours and/or more than a month) standards may be particularly stringent.

Difficult for Recipient to Unpackage

In some cases, it may be inconvenient for the recipient to prepare a drug for delivery and/or to produce a coordinated force to activate a mechanical trigger. For example, the recipient may include a child and/or the medical procedures may induce fatigue or confusion in the recipient (for example chemotherapy). In some cases, the recipient may have a condition that makes it difficult to perform precise tasks (for example rheumatism and/or Parkinson's disease, and/or partial paralysis of the fingers). More generally, opening packaging and then loading the delivery device may be inconvenient and may increase the probability of exposure to contamination or of error or loss of the drug.

Ready—Examples

It is sometimes desirable to supply a recipient with a delivery device that can be stored. It may also be desirable to supply the delivery device ready to use to deliver a medicine. For example, at a certain time following an outpatient hospital procedure, it may be desirable to deliver a drug to the patient (for example an antidote to chemotherapy agent). Sometimes before a hospital procedure, it may be desirable to deliver a drug to a patient (for example a dye before a radiological diagnostic procedure). A recipient may prefer to receive these drugs from a portable drug pump rather than traveling to a clinic.

Minimal Involvement of Recipient

In some embodiments, the apparatus may be supplied with a sealed reservoir having an internal space containing a drug. The apparatus may deliver the drug automatically with minimum involvement of the recipient. Optionally, the delivery apparatus may function independently requiring minimal or no cooperation and/or awareness and/or activity of the recipient. For example, a doctor may attach the device to the recipient and the device may take care of delivery of the drug at the proper time without involvement of the recipient. Alternatively or additionally, a recipient may be given a single packaged device and the recipient may be able to take the drug at the required by merely attaching and activating the device.

Puncture Septum Vial/Syringe

In some embodiments, a drug reservoir may be sealed by a septum. Optionally, unsealing the reservoir may be by puncturing the septum.

In some embodiments, a drug may be packaged in a vial sealed by a septum. Optionally, the septum may be punctured by inserting a hollow needle through the septum into the vial. In some embodiments, the drug may be packaged in a syringe. Optionally, a needle of the syringe may be sealed by an insertion into a septum. Optionally, unsealing may be achieved by pushing the needle of the syringe through the septum.

In some embodiments, unsealing a package includes piercing a septum. The septum may include, for example, many kinds of seals including caps, stoppers, plugs, diaphragms and/or partitions of various thicknesses. For example, a septum or a seal may be made from plastic, rubber, silicone, a gel, a metal foil, a polymer and/or a combination thereof.

Portable and/or Low Profile

Optionally, the apparatus may not require conscious carrying by the recipient. Optionally, the apparatus may minimally disturb the recipient. For example, a pump may be small and/or have a low profile. For example, some embodiments of a drug pump may be worn inconspicuously under a recipient's clothing. The height of the apparatus may be less than the square root of the area of the base.

Optionally, the base of the apparatus may be less than 5 cm long and/or less than 5 cm wide. Optionally, the height of the apparatus may be less than 3 cm. Optionally, the total volume of the apparatus may be less than 100-200 ml. Optionally, the mass of the entire apparatus with the substance may be less than 100-200 g. Optionally, the capacity of the reservoir for the substance in the apparatus may be between 5-30 ml). Optionally, the apparatus may be shock proof and/or waterproof.

The term "reservoir" throughout the specification and claims encompasses any container for a drug, such as but not limited to, a cartridge, vial, syringe, bottle, ampoule and many more, and is not limited to any size or shape. Optionally, the reservoir may be packed and/or stored in the injector. Alternatively or additionally, the reservoir may include a cartridge that is stored separately from the delivery device and inserted into the delivery device at a convenient time.

In some embodiments, the apparatus may be easily disposable (for example in municipal garbage).

Caveats

Caveat about Needles

In some embodiments, the apparatus is a medicine pump. The invention is some embodiments thereof is not limited to a drug pump, and may be used for any kind of suitable discharge apparatus, not just by needle piercing the patient, but also transdermally (wherein the substance is metered by the apparatus to a transdermal patch), by spray (wherein the substance is metered by apparatus to a spray nozzle), micro needles array and others.

Detailed Exemplary Embodiments

General Caveat

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Flow Chart of a Method of Delivery of a Drug

FIG. 1a is a flow chart illustrating an exemplary method of delivering a drug. In the example, it may be preferred that a patient take a drug injection at home and not remain in a medical institution waiting for a nurse to administer the injection. In the exemplary embodiment, the institution is supplied with a portable preloaded automatic apparatus that can be stored until the recipient needs the drug. When the drug is needed, the apparatus is optionally attached to the recipient and/or activated. Optionally, the apparatus takes care of preliminary activities (for example locking a reservoir access door and/or unsealing the drug reservoir and/or inserting a needle into the recipient). The pump then makes the injection and optionally takes care of preparing itself for disposal.

Supply Sloaded Apparatus

In the exemplary embodiment of FIG. 1, the apparatus is optionally supplied 100 to a medical institution. In some embodiments, the injector may be preloaded with the drug and/or preprogrammed. For example, the substance to be injected may be an antidote to a chemotherapy agent to be injected twelve hours after the therapy. Optionally, the antidote is packaged inside the apparatus in a sealed vial. Optionally, the preloaded apparatus may be stored 102 in a medical institution for a time ranging from a few days to a few months before actually being used. Alternatively or additionally, the apparatus may be supplied to the recipient by, for example, a pharmacy and stored by the recipient for a time ranging from a day to a few months until needed. Alternatively or additionally, the sealed vial may be stored separately from the apparatus. Optionally, vial may be loaded into the apparatus by the distributor and/or by a pharmacist and/or by a medical professional (for example a nurse or a doctor) and/or by the recipient himself.

Program Apparatus

In the example of FIG. 1, the apparatus is programmed to deliver the entire contents of the reservoir 12 hours after activation in a constant rate injection. Alternatively or additionally, the apparatus may be programmed to deliver a portion of the medicine in a single dose. Optionally the apparatus may be programmed to administer a second dose. Optionally the second dose may be delivered after a fixed time delay and/or the second dose may be delivered on demand of the recipient and/or upon a combination of time delay and command and/or in reaction to some other stimulus. Optionally, preliminary steps may be preprogrammed into the apparatus logic to be carried out before delivering the medicine. Optionally, the drive train may drive a post injection activity such as injecting a flushing fluid after the medicine.

In some embodiments, a cartridge containing the drug may be stored outside of the injector (for example for an injector that is not preloaded). The cartridge may be inserted into a reservoir channel and/or a door to the channel may be closed 103 before use.

Activate at Hospital

In the example of FIG. 1, when the apparatus is needed, the apparatus is optionally attached 104 to a recipient. Attachment may be, for example by an adhesive pad on a base surface of the housing of the apparatus. After attachment, the apparatus is activated 106. Alternatively or additionally, the apparatus may be activated first and then attached to the recipient.

Unseal then Insert or Vice Versa

Once activated 106, in some embodiments, the apparatus may perform priming 109 before discharging the drug. For example, in some embodiments, priming may include locking 107 a door. For example, the door may be locked when a drive train contacts a locking mechanism. For example, the drive train may expand, filling a space between a door locking mechanism and a plunger. The drive train may optionally expand backwards towards the locking mechanism. The drive train may eventually contact, for example, the locking mechanism causing it to lock. Subsequently, the locking mechanism may, optionally, prevent further backwards motion of the drive train. Further expansion of the drive train may then push the plunger into the reservoir.

For example, priming 109 may include inserting 108 a needle into the recipient. Optionally, at a preprogrammed injection time, the apparatus may insert 108 a needle into the recipient. Alternatively or additionally, the needle may be inserted 108 into the recipient when the injector is activated. Alternatively or additionally, the needle may be inserted 108 into the recipient before locking 107 the door.

Priming 109 may optionally include unsealing 110 the reservoir. For example, the reservoir may include a vial sealed by a septum and the unsealing 110 include puncturing the septum. Alternatively or additionally, inserting the needle into the recipient may follow and/or precede unsealing the reservoir.

Delay Between Unseal and Inject

In some embodiments, inserting 108 a needle into the recipient and unsealing 110 the reservoir may open a fluid path between the reservoir and the recipient. Once the fluid path is open, the drug may optionally be discharged 112 into the recipient at a dosage and rate that is optionally controlled by a controller of the injection apparatus.

In some embodiments, discharge 112 of the drug will start quickly after unsealing 110 the reservoir and/or inserting 108 the needle. For example, in some embodiments discharging 112 will start less than 5 minutes after inserting 108 and/or unsealing 110. In some embodiments, discharging 112 will start less than one minute after inserting 108 and/or unsealing 110. In some embodiments, there may be a short delay after unsealing 110 the reservoir and/or inserting 108 the needle before discharging 112 the substance. In some embodiments, the delay may range between 30 seconds and 5 minutes.

Post Injection Activities Chaser/Deactivate

In some embodiments, the apparatus may perform post injection tasks. For example, after the drug has been fully or partially discharged 112, an optional chaser of for example saline solution may be injected. The apparatus may optionally be automatically permanently deactivated 114. For example, deactivation may include retracting the needle. Once the apparatus is deactivated, it may be removed 116 from the recipient and discarded 118. Additionally or alternatively, the apparatus may be removed from the recipient and then disabled. For example, upon removal of an injection apparatus, the needle may be retracted and/or a cover may be deployed to protect the needle.

Single Motion

In some embodiments, some or all of insertion 108 of the needle and/or unsealing 110 of the reservoir and/or discharging 112 and/or deactivation 114 of the apparatus may be triggered and/or driven by a single motion drive train. For example, the drive train may include an electric motor and/or a screw and/or a piston. The motion may optionally be continuous. Alternatively or additionally, the injector may be programmed by the distributor and/or medical personnel (for example a nurse, a doctor or a pharmacist) and/or by the recipient.

An External View of an Exemplary Low Profile Drug Injector

Low Profile

Figure 2A:
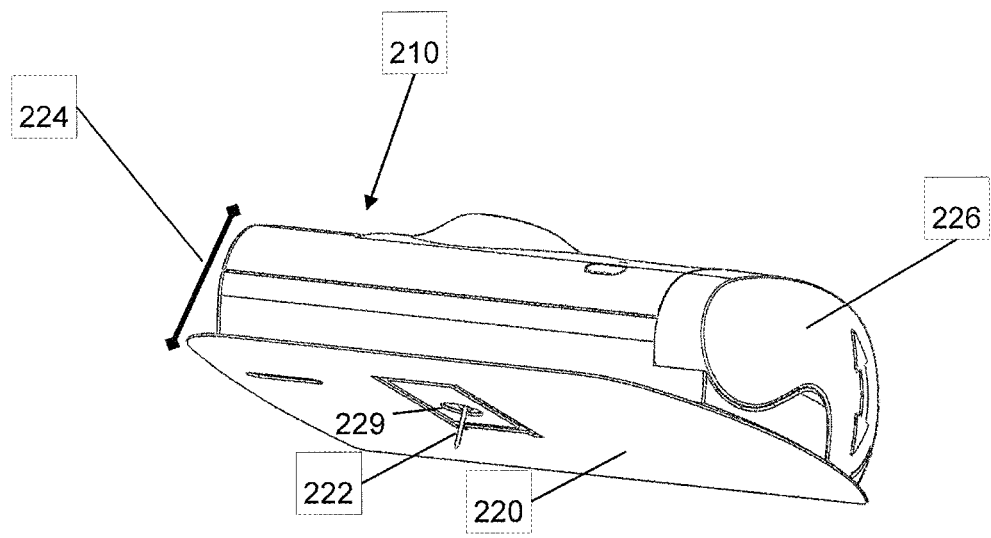
FIG. 2a is a perspective external view of an exemplary embodiment of an apparatus for puncturing a septum and delivering a drug.

FIG. 2a illustrates an external view of an exemplary embodiment 210 of a drug delivery apparatus (a subcutaneous injector apparatus). During use of embodiment 210, a base surface 220 is stuck to the recipient's skin with an adhesive. A needle 222 extends out a needle opening 229 into a recipient. The drug is discharged via needle 222 into the recipient. Optionally, embodiment 210 is has a large base 220 (for example, the length and width of base 220 is 4 cm by 6 cm) and a low profile (for example, the height 224 of the apparatus is 2 cm). In exemplary embodiment 210, height 224 of the apparatus is less than half the square root of the surface area of base 220. In some embodiments, the height may be less the 1.4 times the square root of the surface area of the base. Embodiment 210 may be stabile when stuck to the recipient's skin. Embodiment 210 may be inconspicuous when worn under clothing.

Tamper Proof Lock—Reuse

A locking door 226 may optionally be provided. In a closed position, door 226 may for example, block a reservoir channel. For example, door 226 may prevent tampering with the drugs inside the injector. It is noted that although embodiment 210 is typically a one-use item, the electronics, batteries and motor and other elements of the system can be used more than once if desired. Locking may occur immediately upon closing door 226 and/or door 226 may be locked after activation of the injector.

Figure 2B:
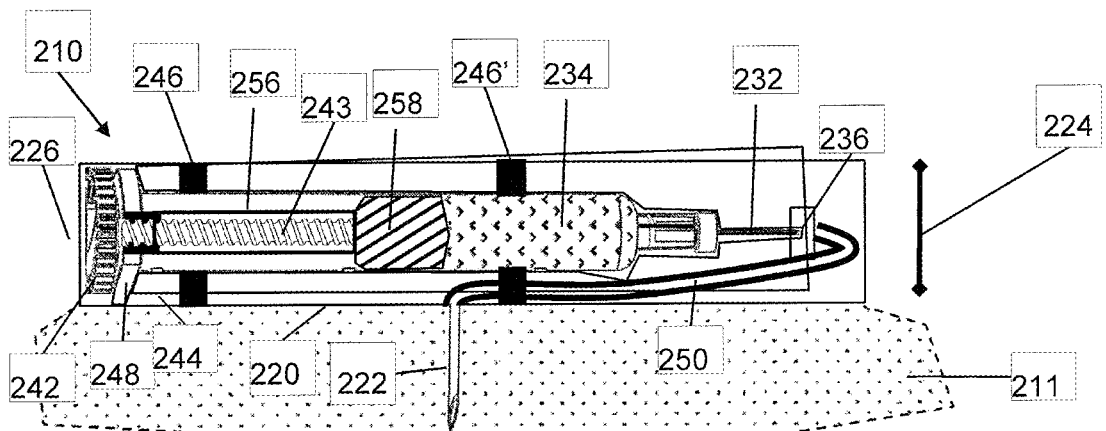
FIG. 2b is a simplified cutaway view of an exemplary embodiment of an apparatus for puncturing a septum and delivering a drug prior to puncturing the septum.
Figure 2C:
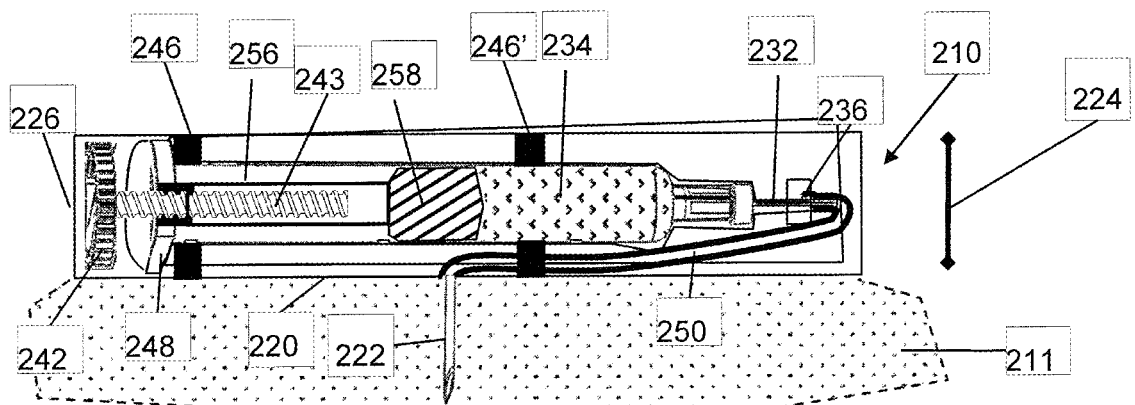
FIG. 2c is a simplified cutaway view of the embodiment of FIG. 2b after puncturing the septum.
Figure 2D:
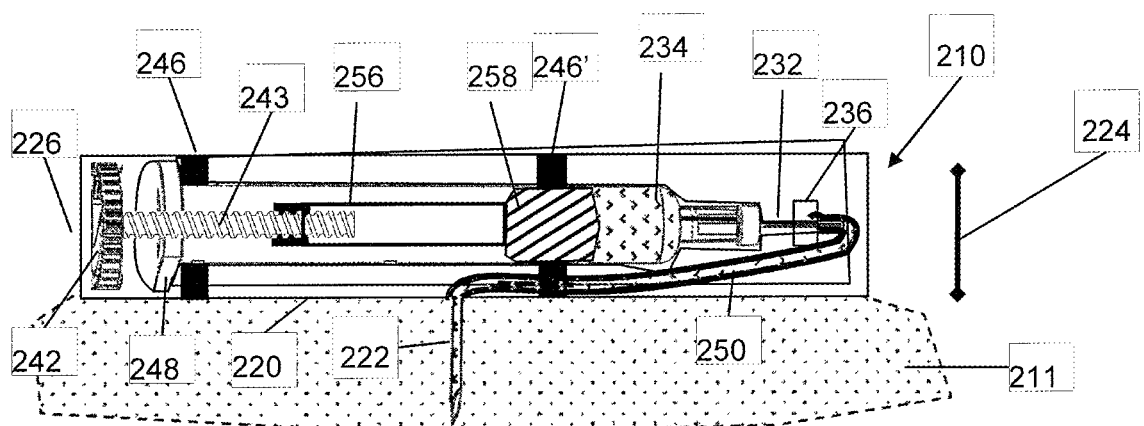
FIG. 2d is a simplified cutaway view of the embodiment of FIG. 2b while delivering the drug.

A Schematic Illustration of an Exemplary Drug Pump Having a Septum Puncturing Mechanism FIGS. 2b-d are schematic cutaway side views illustrating exemplary embodiment 210 of a drug delivery apparatus puncturing a septum and delivering a drug.

FIG. 2b illustrates exemplary embodiment 210 in an initial state. In the example, base 220 of the apparatus is attached to the flesh 211 of a recipient. Hypodermic needle 222 protrudes from base 220 of the apparatus into the flesh 211 of the recipient. Optionally, hypodermic needle 222 may be inserted into the recipient by a release mechanism. In some embodiments, needle 222 protrudes perpendicular to base 220.

In the example, a reservoir 234 is in fluid contact with a hollow needle 232. Optionally, reservoir 234 and consequently needle 232 are held in place, using low friction pads 246 and 246'. In the example, in the initial state, reservoir 234 is placed towards the rear (left side) of the apparatus so that there is a gap 244 between a flange 248 of reservoir 234 and pad 246. In the initial state, needle 232 and consequently reservoir 234 are sealed by a septum 236.

Some embodiments may include a drive train 256 that translates circular motion of a gear 242 into translational motion. For example, drive train 256 may include a mechanical actuator, which causes backward and/or forward motion along a single path, for example a straight line. For example, drive train 256 may include a telescoping assembly. In the exemplary embodiment, activating a motor supplies a torque to turn gear 242 and screw 243. Optionally, the housing of the apparatus prevents translation motion of gear 242 and screw 243.

In some embodiments, rotation of screw 243 causes drive train 256 to telescope. While reservoir 234 is sealed, drive train 256 pushes reservoir 234 along a linear path of motion parallel to base 220 of the apparatus. Needle 232 may optionally be located along the path of motion of drive train 256. Needle 232 may be directed along the path of motion of drive train 256. Needle 232 may optionally be pointed toward septum 236. Expansion of drive train 256 advances needle 232 through septum 236. Eventually, needle 232 pierces septum 236, unsealing reservoir 234 as shown, for example, in FIG. 2c.

In embodiment 210, the motion of drive train 256 and/or reservoir 234 may be parallel to the base of the apparatus. In embodiment 210, the path of motion of a plunger 258 is parallel to the base of the apparatus. In embodiment 210, the long axis of reservoir 234 is parallel to the base of the apparatus. The Length of base 220 of exemplary embodiment 210 is longer than the height 224 of the apparatus. In some embodiments, the long axis of and/or the pathway followed by reservoir 234 may be directed non-parallel to and/or orthogonal to hypodermic needle 222.

In FIG. 2c, the exemplary embodiment is shown with needle 232 puncturing septum 236. In the example, flange 248 is in contact with pad 246 stopping further forward movement of reservoir 234.

In some embodiments, puncturing septum 236 creates a fluid pathway from reservoir 234 through hollow needle 232 and through a canal 250 and through hypodermic needle 222 to flesh 211 of the recipient.

In the exemplary configuration of FIG. 2c, further, drive train 256 advances a plunger 258 inside of reservoir 234 as illustrated, for example, in FIG. 2d. Advancement of plunger 258 discharges the drug out of needle 232, canal 250 and needle 222 into flesh 211 of the recipient.

Figure 3:
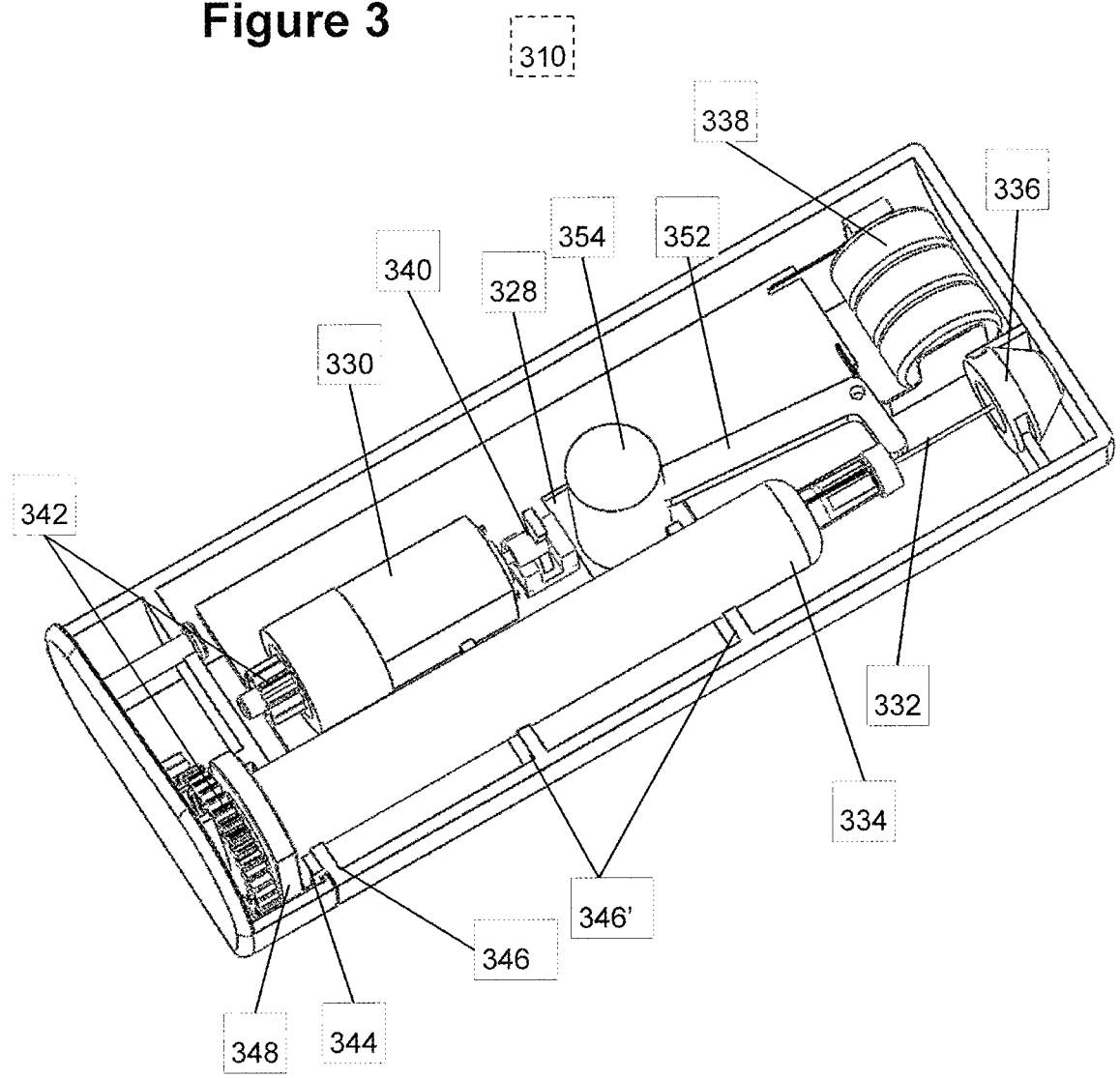
FIG. 3 is a perspective view of the mechanism of another exemplary embodiment of an apparatus for delivering a drug wherein a septum seals a needle prior to puncturing the septum.
Figure 3:
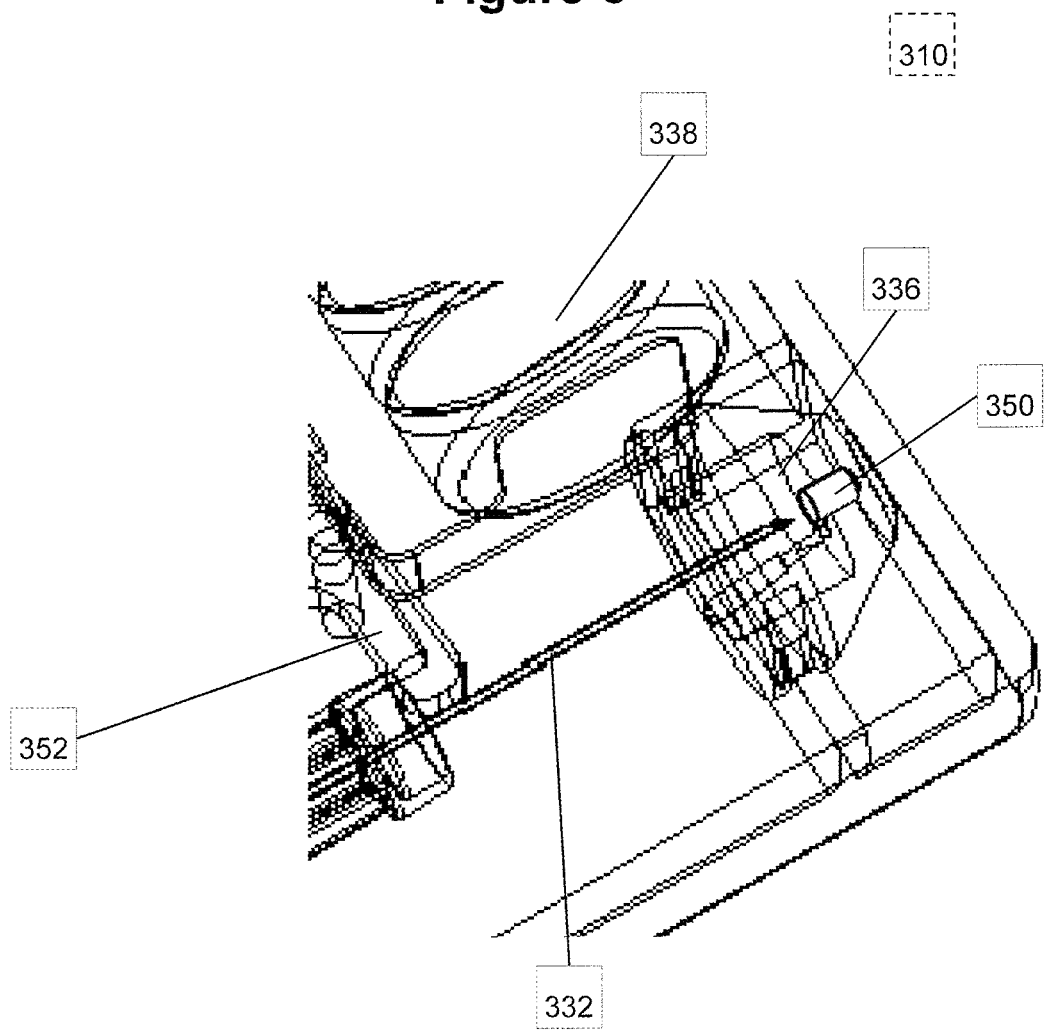

An Exemplary Syringe Reservoir with a Needle for Puncturing a Septum FIGS. 3, 3', 4 and 4' illustrate another exemplary embodiment 310 of a drug delivery apparatus. In embodiment 310, a syringe needle 332 is mounted to a reservoir 334. In FIGS. 3 and 3' needle 332 is shown sealed by an optional septum 336. In FIGS. 4 and 4' needle 332 is shown puncturing septum 336 to unseal reservoir 334.

FIGS. 3 and 4 illustrate an optional programmable controller 328 capable of directing an optional actuator 330 for powering discharging of a substance. In addition, FIGS. 3, 3', 4 and 4' illustrate how actuator 330 may optionally drive puncturing of septum 336 and/or trigger insertion of a needle into the recipient.

Programmable

In some embodiments, controller 328 may be a programmable electronic processor. Controller 328 may optionally include a memory.

In some embodiments, actuator 330 may include a direct current (DC) electric motor. Power for controller 328 and actuator 330 may be supplied by a power supply 338 (for example batteries). Controller 328 may optionally direct actuator 330 by pulse width modulation (PWM). Alternatively or additionally, actuator 330 may include a brushless DC servo (for example a stepper motor) directed by controller 328. In some embodiments, the rate of rotation of actuator 330 may be adjustable. The rate of discharge of the drug may correspond to the rate of rotation of the actuator 330. Optionally, rate of rotation of the actuator 330 may be adjusted by programming controller 328 and/or by a user interface (for example a dial and/or button) on the apparatus.

Detect Fault e.g. Failure to Move

Embodiment 310 includes an optimal rotation sensor 340. In some embodiments rotation sensor 340 may include an optical sensor that detects movements of a paddle. Alternatively or additionally, rotation sensor may include a Hall Effect sensor or the like. Optionally, if actuator 330 fails to rotate and/or rotates too slowly upon application of power, controller 328 may notify the recipient of a malfunction. Other malfunctions that may be detected include not enough voltage, not enough current, too much current, and/or too fast rotation.

Needle Mounted to Reservoir Sealed by Septum

In FIGS. 3 and 3', a drug reservoir 334 is shown in a sealed configuration. Reservoir 334 is held in place for example by low friction pads 346 and 346'. In the sealed configuration, needle 332 is optionally sealed by septum 336, for example, as illustrated in FIG. 3'.

In some embodiments, when reservoir 334 is in the sealed configuration, a gap 344 exists between a flange 348 of reservoir 334 and friction pad 346.

Pump Mechanism Puncture Septum

Figure 5:
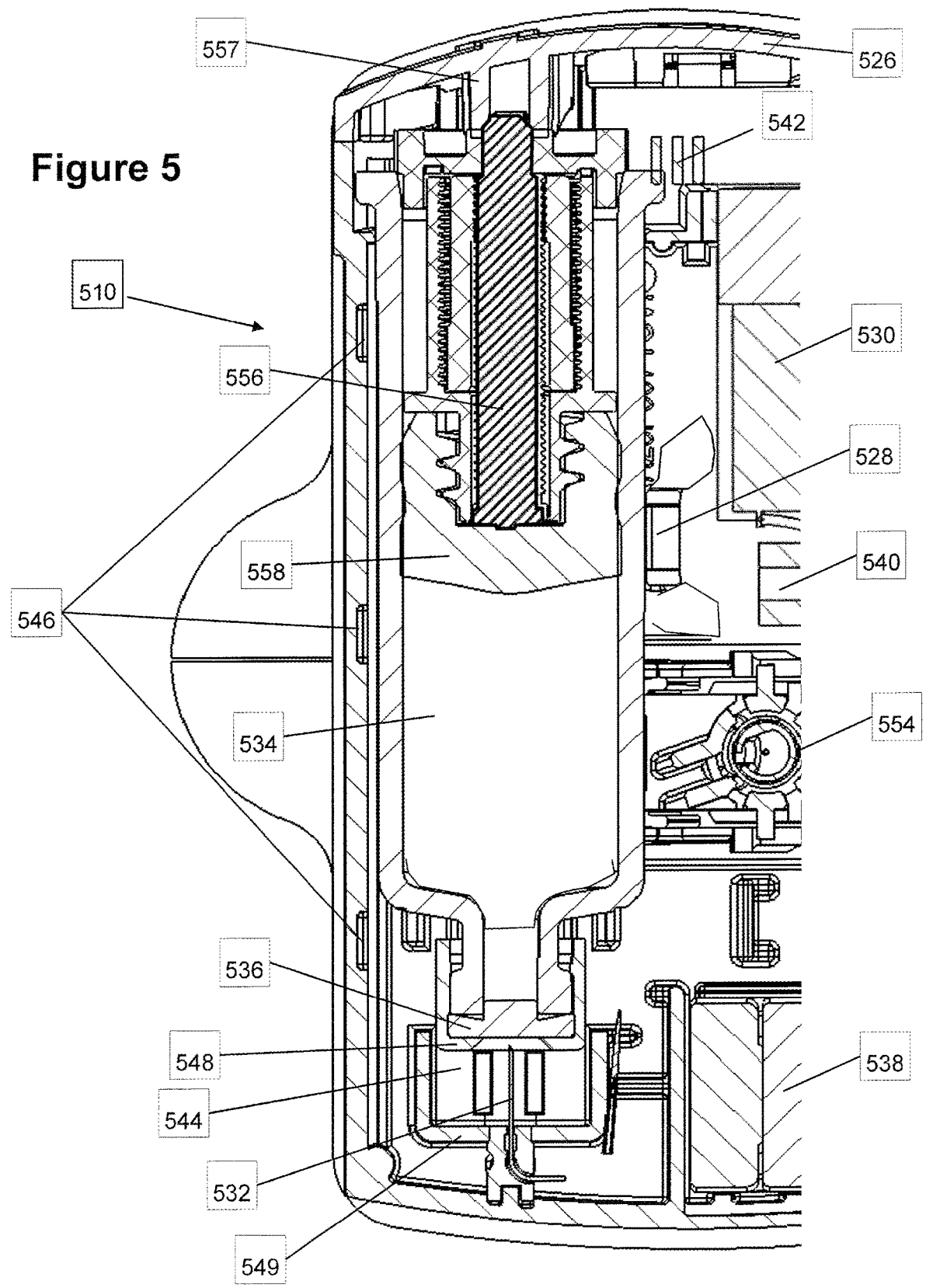
FIG. 5 is a cutaway view of a further exemplary embodiment of an apparatus for delivering a drug wherein a septum seals a vial prior to puncturing the septum.
Figure 6:
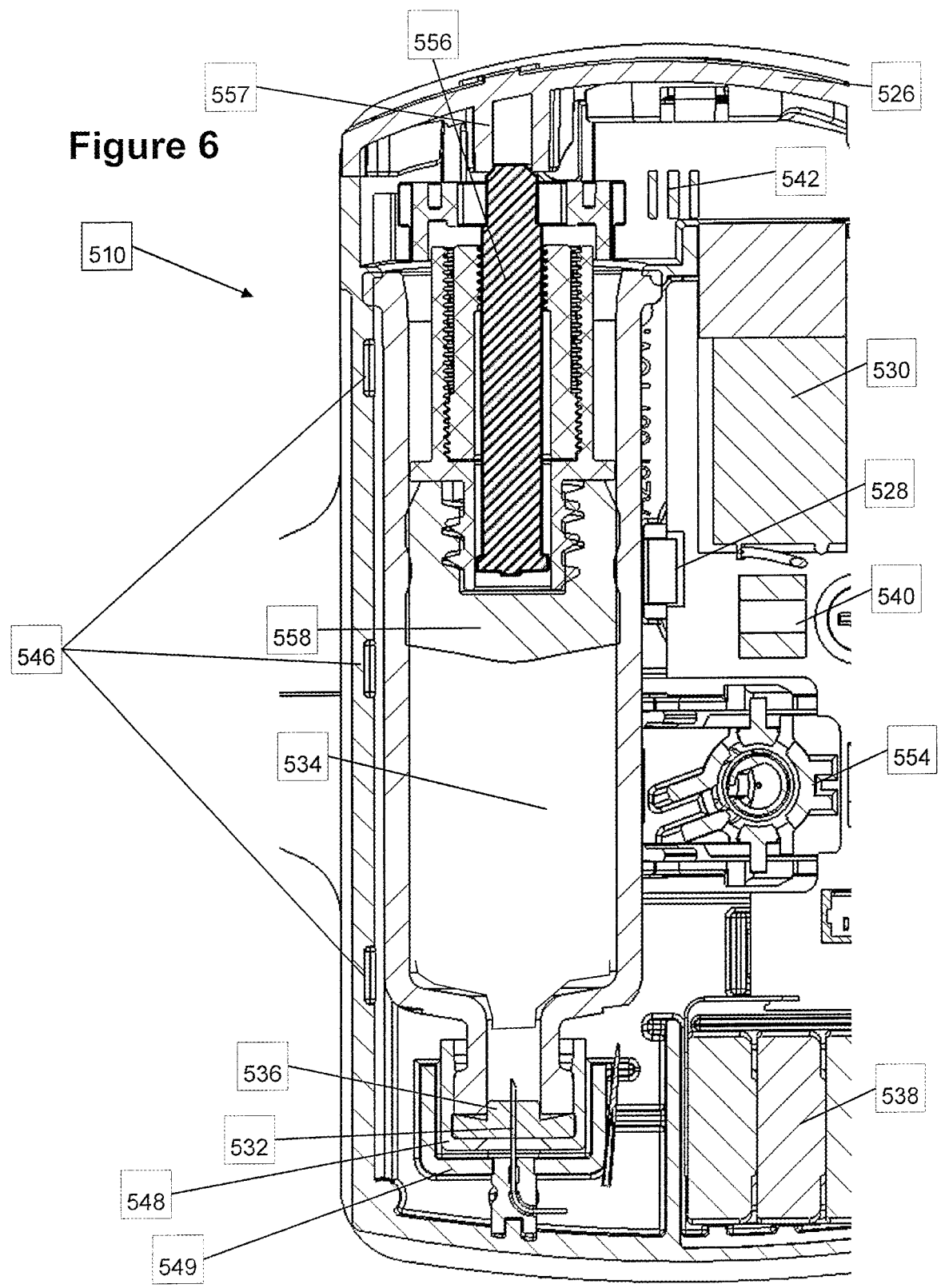
FIG. 6 is a cutaway view of the embodiment of FIG. 5 after puncturing the septum.

In some embodiments, a transmission including gears 342 which connect actuator 330 to a telescoping drive train (for example see drive train 456 FIG. 4) located inside reservoir 334. A more detailed view of an exemplary embodiment of a drive train 556 is shown in FIGS. 5 and 6. For example, drive train 556 may include a telescoping assembly. For example, the telescoping assembly may include one or more concentric screw threads and/or a gear. For example, the telescoping assembly may convert rotational motion into linear expansion and/or contraction of the assembly. Alternatively or additionally, a drive train may include a linear actuator. In exemplary embodiment 310, the transmission includes a gear, but alternatively or additionally, it could include another coupling element for transmitting rotary motion, such as a friction wheel. Optionally rotation of actuator 330 drives expansion of telescoping drive train 456. Alternatively or additionally, the drive mechanism may include an expanding gas chamber. For example, expanding gas may be produced by an electrolytic cell and/or by a chemical reaction. Alternatively or additionally, the reservoir may have flexible walls. Optionally, discharge may include deforming and/or squeezing the reservoir.

In embodiment 310, while reservoir 334 is in the sealed configuration of FIGS. 3 and 3', expansion of drive train 456 drives reservoir 334 and needle 332 forward. Optionally, forward motion stops when flange 348 contacts friction pad 346, which acts as a stop along the path of motion of reservoir 334.

In some embodiments, forward movement of reservoir 334 pushes needle 332 through septum 336 putting the apparatus into the discharge configuration, for example, as illustrated in FIG. 4. In the discharge configuration, a gap 444 has formed behind flange 348. The rear end of telescoping drive train 456 can be seen in gap 444. In the discharge configuration, needle 332 has fully punctured septum 336, unsealing reservoir 334. A fluid path exists from reservoir 334 through needle 332 to a canal 350.

In embodiment 310, the path of motion of reservoir 334 is parallel to the base of the apparatus. In embodiment 310, the path of motion of drive train 456 is parallel to the base of the apparatus. In embodiment 310, the long axis of reservoir 334 is parallel to the base of the apparatus. The base of the apparatus is longer than the height of the apparatus.

Insert Needle Before/after Septum

Embodiment 310 includes an optional trigger arm 352 for triggering a needle release 354. As reservoir 334 moves forward it displaces arm 352 causing needle release 354 to insert a hypodermic needle (not shown) into the recipient. A tube (not shown) supplies a fluid pathway from canal 350 to the hypodermic needle. In the discharge configuration, there is a fluid pathway from reservoir 334 to the recipient. Optionally, the hypodermic needle may be inserted into the recipient either before or after completing puncturing of septum 336. Alternatively or additionally, controller 328 may directly control needle release 354. Optionally, the direction of release of the needle may be non-parallel and/or orthogonal to the direction of movement of drive train 456.

Measure Flow/Know Status

In the example of embodiment 310, telescoping drive train 456 includes a threaded member to convert rotational motion of actuator 330 into expansion and translational motion of the drive train 456. Optionally, in embodiment 310 rotation of sensor 340 may be directly proportional translational movement. In embodiment 310, measurements of rotation can be used to sense the position of the translational mechanism. By means of measurements of the rotation of actuator 330, controller 328 optionally tracks the location of telescoping drive train 456 and/or of reservoir 334 and/or of needle 332. Optionally the rate of discharge of the drug may be detected by measuring a rate of rotation of sensor 340. Optionally, the state of the septum 336 (for example whether drive train 456 has advanced far enough to puncture septum 336) and/or the cumulative volume of medicine discharged may be sensed based on the cumulative number of revolutions of rotation sensor 340.

Discharge

In embodiments 310, when reservoir 334 is in the discharge configuration, friction pad 346 prevents further forward motion of reservoir 334. As stated above, in the discharge configuration, there is a fluid flow path from reservoir 334 into the recipient. Further expansion of the drive train 456 impels a plunger into reservoir 334 discharging the contents of reservoir 334 out needle 332 into canal 350 and out canal 350 through the hypodermic needle into the recipient.

A Reservoir where a Hollow Needle is Inserted into a Vial Through a Septum

FIG. 5 is a cutaway illustration of an exemplary embodiment 510 of a drug delivery apparatus. In embodiment 510, a reservoir is sealed by a septum. Optionally, the septum is punctured by driving the reservoir toward a hollow needle until the point of the needle punctures the septum. Upon puncturing the septum, the point of the needle enters the reservoir. Subsequently, the hollow of the needle provides for fluid communication between the reservoir and the external environment.

Embodiment 510 includes a reservoir 534 sealed by a septum 536. Optionally, reservoir 534 may be placed a bit away from a hollow needle 532 in a sealed configuration (For example, as illustrated in FIG. 5). Reservoir 534 may be held in place, for example, using low friction pads 546, with needle 532 against and/or partially inserted into and/or adjacent to septum 536.

In embodiment 510, activating a motor 530 may cause a drive train 556 to telescope. Rearward movement of drive train 556 may optionally be restrained by a hub 557 mounted on a door 526. Telescoping drive train 556 may push a plunger 558 into reservoir 534. In the example of embodiment 510, telescoping drive train 556 includes concentrically mounted threaded members to convert rotational motion of an actuator, motor 530, into expansion of drive train 556 and translation of plunger 558. Because reservoir 534 is sealed, translation of plunger 558 advances reservoir 534 against needle 532, puncturing septum 536 (as shown, for example, if FIG. 6). Optionally, reservoir 534 translates forward until a cap 548 of reservoir 534 crosses a gap 544 and contacts a stop 549.

Puncturing septum 536 creates a fluid flow path between reservoir 534 and the recipient's body. The flow path allows further translation of plunger 558 to produce fluid flow out needle 532 and through a tube (not shown) into a hypodermic needle (not shown) and into the recipient.

Embodiment 510 includes further optional components, for example, batteries 538, and a needle release 554, and a rotation sensor 540, and a controller 528, and a transmission 542.

A Septum Preserving Aseptic Conditions of a Hypodermic Needle

Figure 7A:
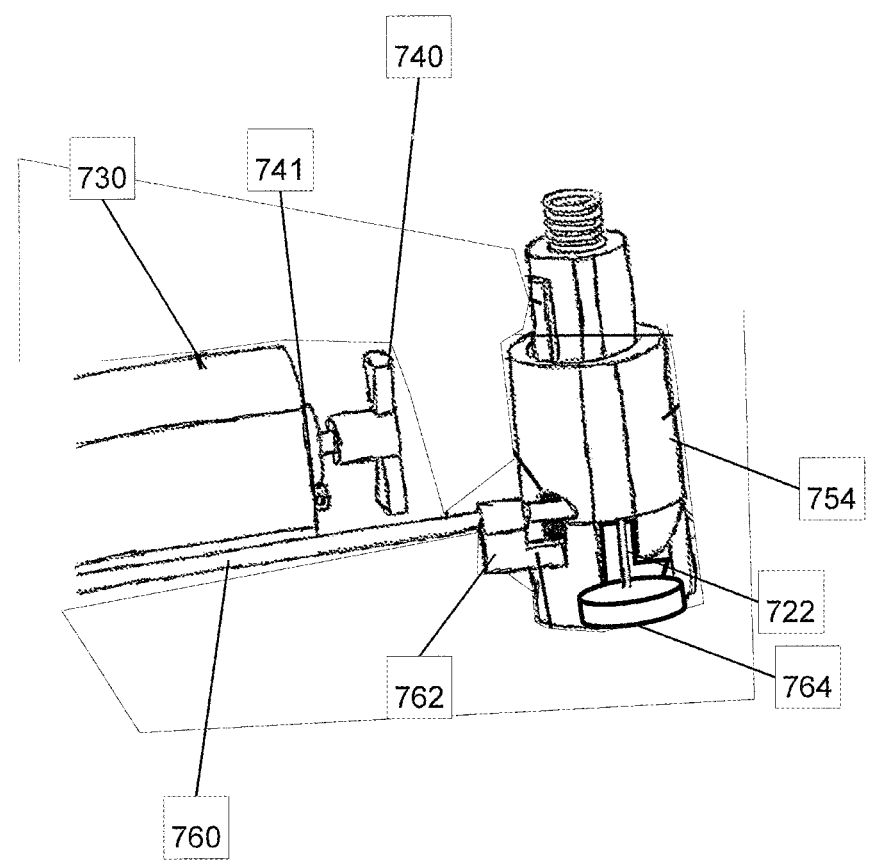
FIG. 7a illustrates a perspective view of an exemplary embodiment of a needle insertion mechanism with a septum, prior to releasing the needle.
Figure 7B:
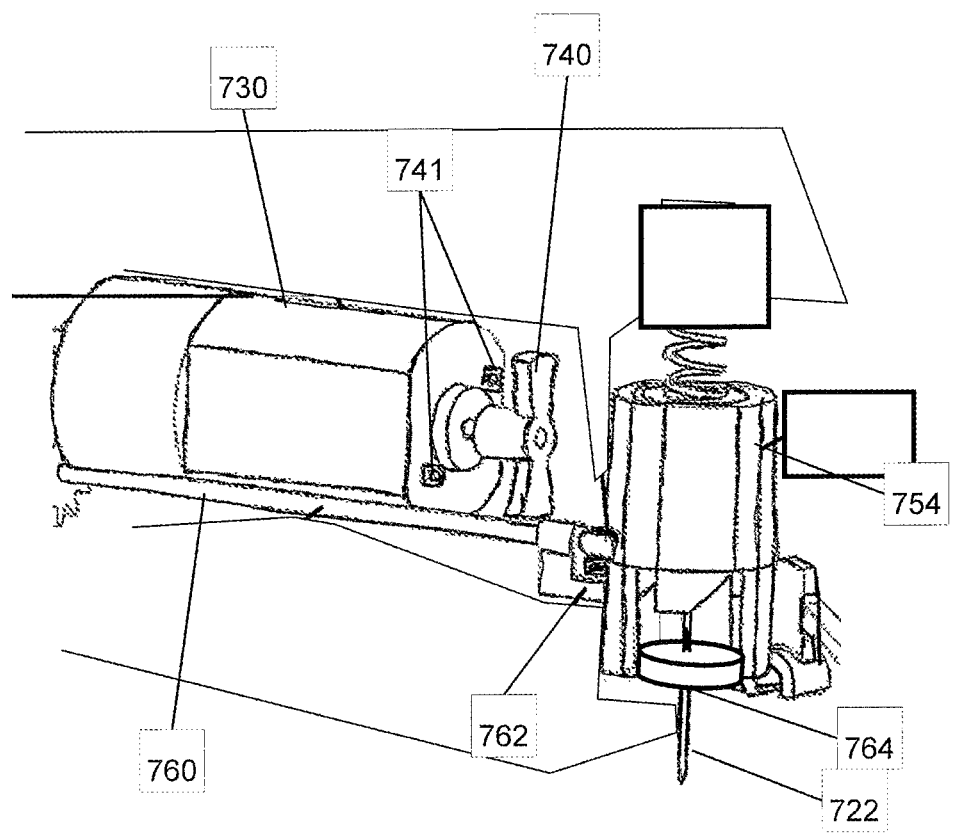
FIG. 7b illustrates a perspective view of an exemplary embodiment of a needle insertion mechanism with a septum after releasing of the needle.

FIGS. 7a and 7b illustrate perspective views of an exemplary embodiment of a needle insertion mechanism 754 with a needle opening septum 764. Needle opening septum 764, seals a needle opening, preserving aseptic conditions inside an injector (as illustrated, for example, in FIG. 7c).

In some embodiments, when the apparatus is attached to a recipient, when needle 722 is released, it may optionally pass through needle opening septum 764 (as illustrated, for example, in FIG. 7b) and be inserted into the flesh of the recipient.

In some embodiments, prior to release, needle 722 may be partially inserted into needle opening septum 764 (for example as illustrated in FIG. 7a). While partially inserted, the opening at the tip of needle 722 may be sealed by needle opening septum 764. Needle 722 may be in fluid communication with a drug reservoir. Sealing needle 722 may seal the reservoir. Alternatively or additionally, prior to release, a hypodermic needle 722' may be held clear of a needle opening septum 764', as illustrated, for example in FIG. 7c.

In the example of FIGS. 7a,b a motor 730 rotates a shaft 760. Rotation of shaft 760 optionally causes a threaded arrester 762 to slide out of an opening in insertion mechanism 754 releasing needle 722. In some embodiments, motor 730 may also trigger unsealing a reservoir and discharging of a drug (as illustrated, for example, above). An optional rotation sensor includes sensors 741, which sense revolutions of a paddle 740.

Figure 7C:
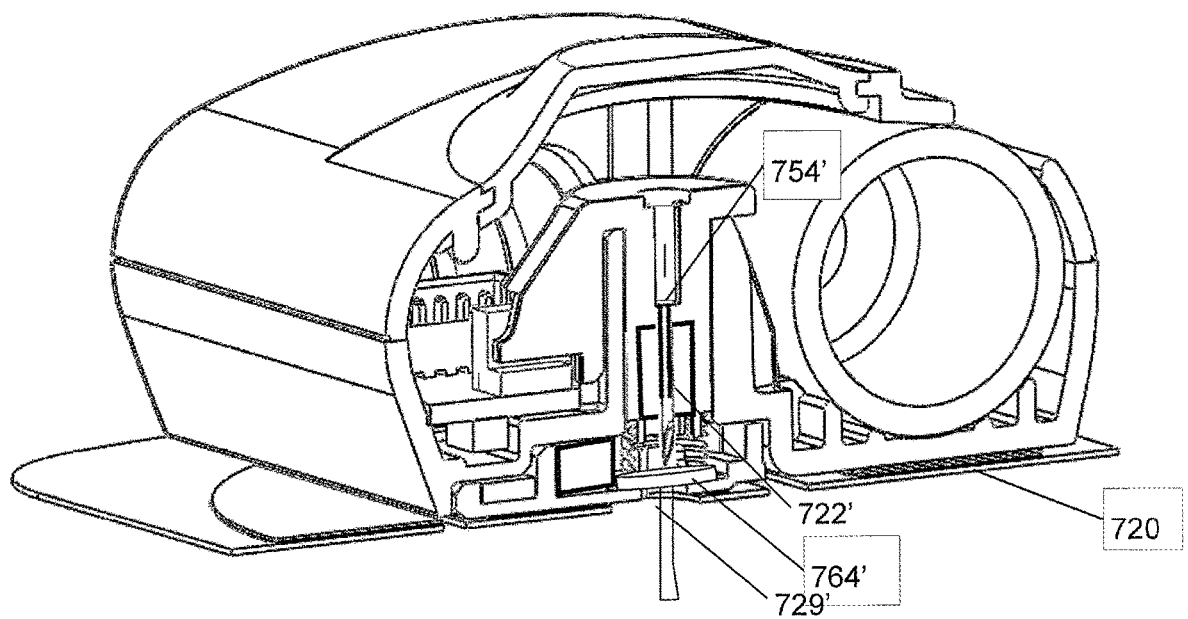
FIG. 7c illustrates a cutaway perspective view of an exemplary embodiment of an injection apparatus with a septum and a needle release, previous to releasing the needle.
Figure 7D:
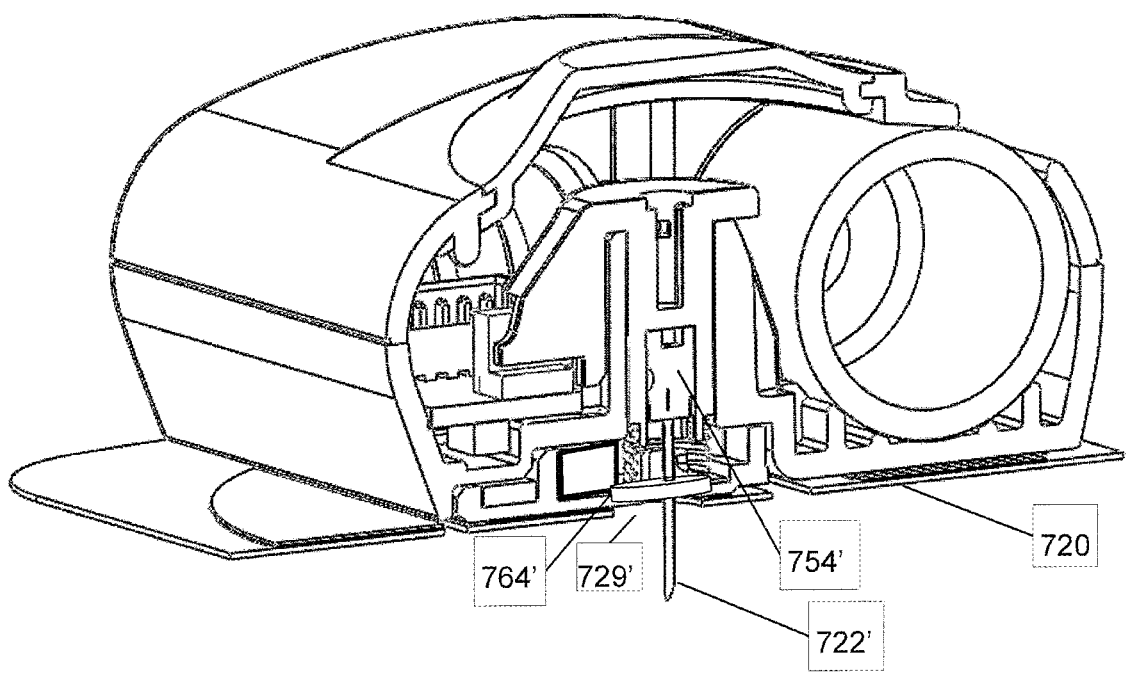
FIG. 7d illustrates a cutaway perspective view of an exemplary embodiment of a injection apparatus with a septum and a needle release, after releasing the needle.

In some embodiments, needle opening septum 764' may be fixed to the housing of the injection apparatus. For example, FIGS. 7c and 7d are cutaway perspective illustrations of an exemplary embodiment where needle opening septum 764' is connected to a base 720 of the housing of the injection apparatus. FIG. 7c illustrates the exemplary embodiment prior to release of a needle 722' by a release 754'. In the illustration, needle opening 729' is sealed by needle opening septum 764'. FIG. 7d illustrates the exemplary embodiment after release of needle 722' and after needle 722' punctures needle opening septum 764'.

Figure 8:
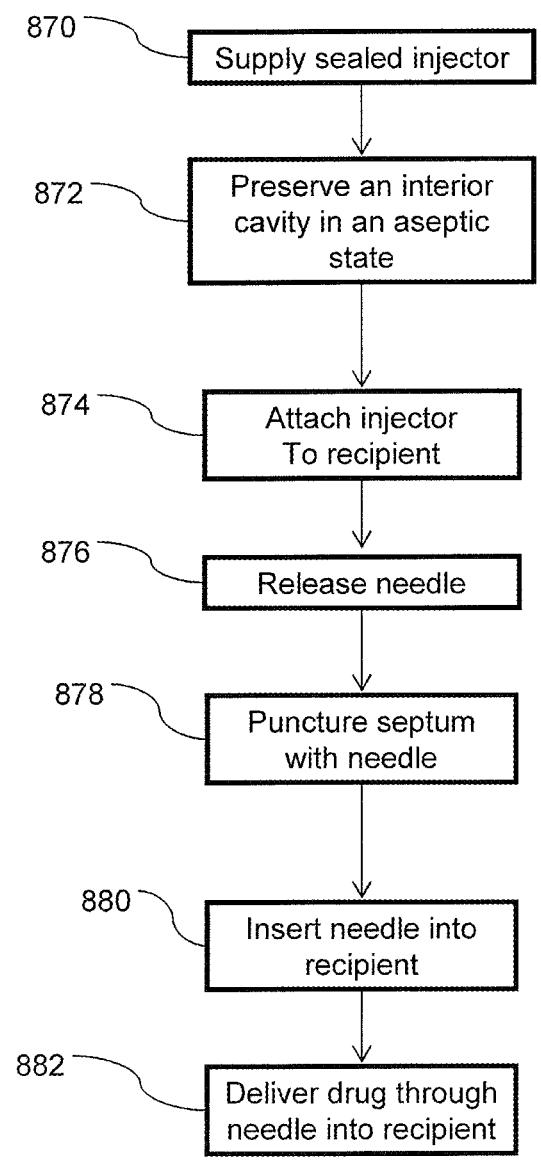
FIG. 8 is a flowchart illustrating an exemplary embodiment of a method for delivering a drug to a recipient with an initially sealed injector.

FIG. 8 is a flow chart illustration of an exemplary embodiment of a method for delivering a drug to a recipient. In some embodiments, an injector apparatus may be supplied 870 in a sealed state. Optionally in the sealed state, an internal space of the injector may be preserved 872 in an aseptic state by a septum and/or by a sealed door. Optionally, a hypodermic needle may be stored in the aseptic internal space of the injector. Alternatively or additionally, an injector and/or the cartridge may be supplied in a sealed aseptic blister. In the blister, the injector may optionally be supplied in an open and/or closed state.

In some embodiments, the apparatus may be attached 874 to the recipient while still in the sealed state. For example, a base of the apparatus may be stuck to the recipient using an adhesive.

In some embodiments, there may be a release mechanism. The mechanism may release 876 the needle. For example, the needle may be released 876 after attachment 874 of the apparatus to the recipient. Optionally upon release 876, the needle may puncture 878 the septum.

In some embodiments, the needle may continue through the septum, through a needle opening in the base of the apparatus and be inserted 880 into the recipient.

Once the needle is inside the recipient, a drug may optionally be delivered 882 through the needle into the recipient.

Door Locking Mechanisms

Figure 9A:
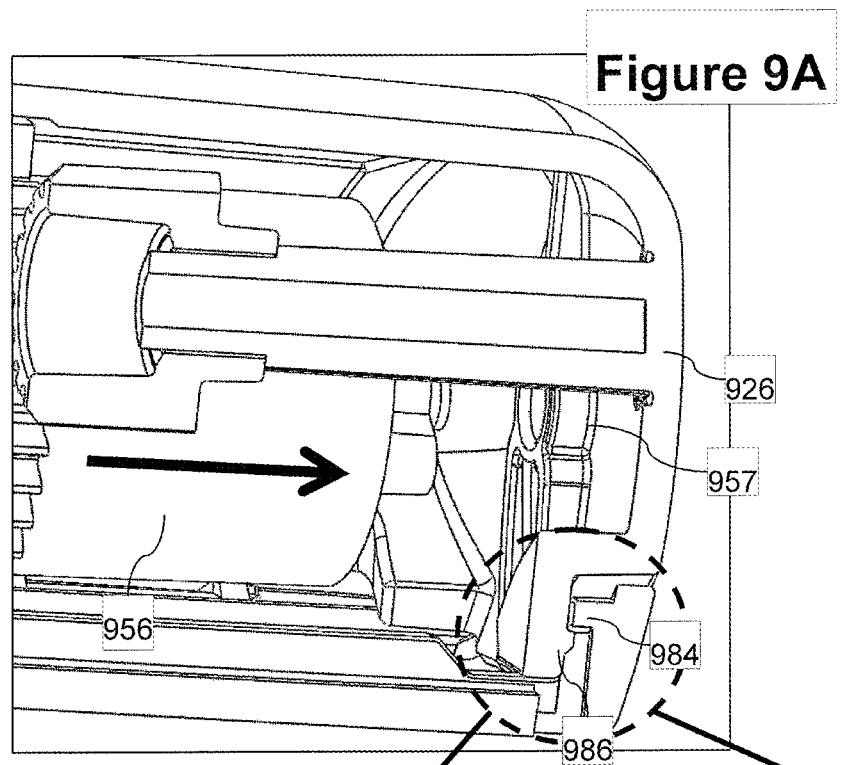
FIGS. 9A,B illustrate an exemplary pressure activated door latch locking mechanism in accordance with an embodiment of the present invention.
Figure 9B:
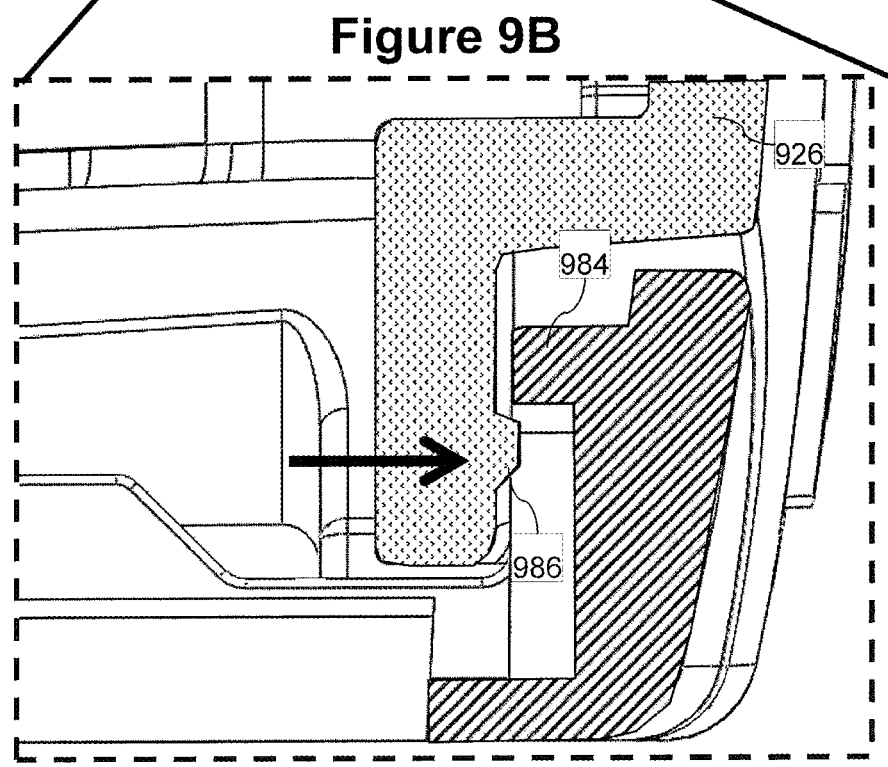

FIGS. 9A and 9A illustrate respective wide and close up cutaway views of an exemplary embodiment of a mechanism locking a door of an infuser. For example, a door may include a latch that may engage catch in the housing of the infuser, locking the door closed. Optionally, the door and/or the latch may be biased away from the catch and/or play in the door may allow the latch to be disengaged from the catch. In some embodiments, activation of the drive train may drive the latch into engagement with the catch, locking the door.

In some embodiments, the drive train may include a telescoping assembly. The telescoping assembly may optionally be attached at its front end to a plunger in a medicine reservoir. Behind the telescoping assembly, there may optionally be some free space and/or a door. As the telescoping assembly expands, it may fill the free space and then optionally push backwards against the door and forward against the reservoir. In some embodiments, pushing the door backwards may cause engagement of the latch and the catch. Further rearward movement may optionally be restrained by the door and/or the latch. In some embodiments, pushing forward against the reservoir may cause unsealing of the reservoir. Forward movement of the reservoir may optionally be restrained by contact between a flange and/or a front end of the reservoir with the housing. Further, expansion of the telescoping assembly may, in some embodiments, force the plunger into the reservoir, discharging the medicine.

In some embodiments, a latching mechanism may include, a hub 957 and/or a latch 986 and/or a catch 984. Latch 986 may optionally be configured to engage catch 984 holding door 986 immobile with respect to the housing of the infuser. Door 926 may optionally be configured to swing upward and/or downward around a pivot. Closing the door may, for example, block access to a reservoir channel. The mounting of door 926 may leave slack allowing forward and backward movement of the door engaging and/or disengaging latch 986 with catch 984.

In some embodiments, activating the apparatus may drive a rear end of a drive train 956 into hub 957. This may, optionally, drive door 926 backwards taking up the slack in its movement. Driving door 926 backwards may, for example, force latch 986 into engagement with catch 984 thereby preventing door 926 from swinging upward. This may, optionally, permanently lock door 926.

In some embodiments, the slack in the door may range between, for example, 0.1 and 3 mm.

FIGS. 10A-D illustrate a second exemplary embodiment of a locking mechanism for an infuser. The locking mechanism of FIGS. 10A-D may optionally include a temporary latch and/or a permanent latch. Upon closing a door, the temporary latch may optionally hold the door closed. In some embodiments, a user may be able to disengage the temporary latch. For example by pushing sideways on a tab, may release the temporary latch and open the door. Upon activating the infuser, a drive train may optionally drive engagement of a permanent locking mechanism. For example, the permanent locking mechanism may prevent disengagement of the latch.

Figure 10A:
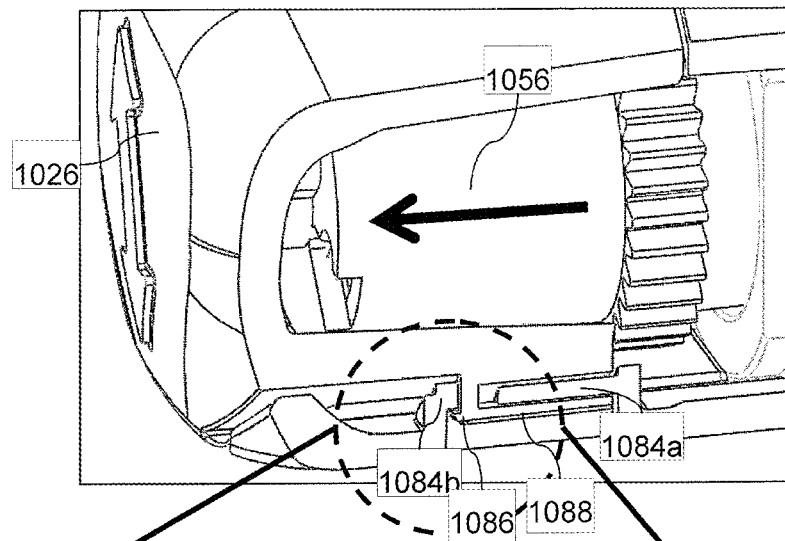
FIGS. 10A,B,B',C,D,D',D" illustrate an alternative exemplary pressure activated door latch locking mechanism in accordance with an embodiment of the present invention.
Figure 10B:
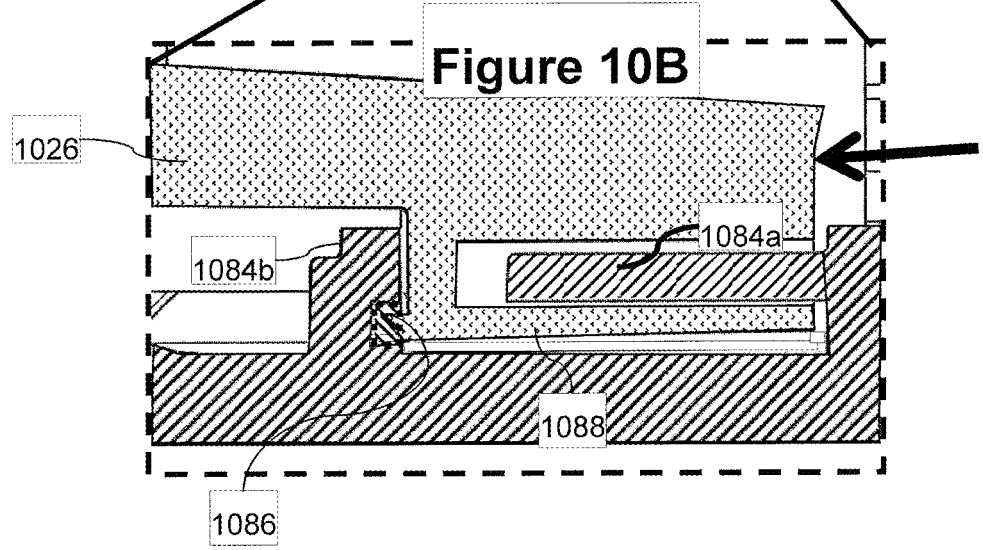
Figure 10B:
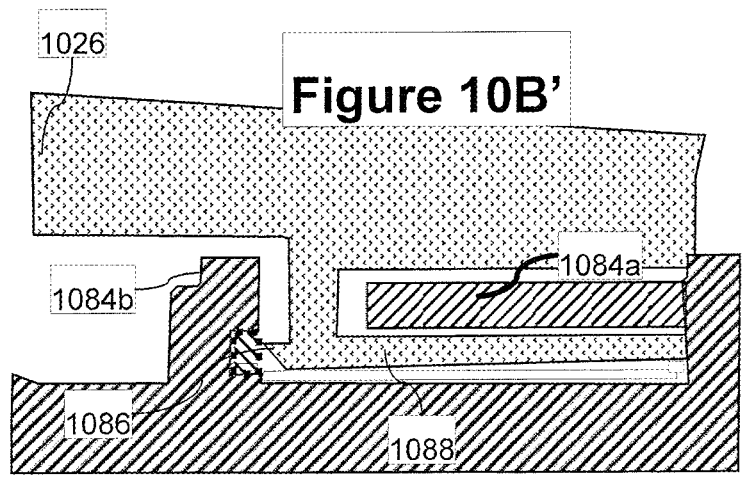
Figure 10C:
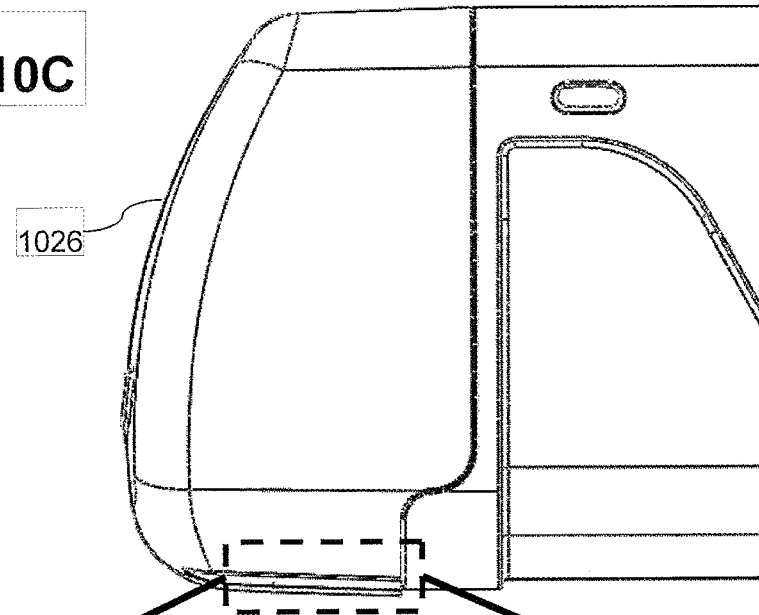
Figure 10D:
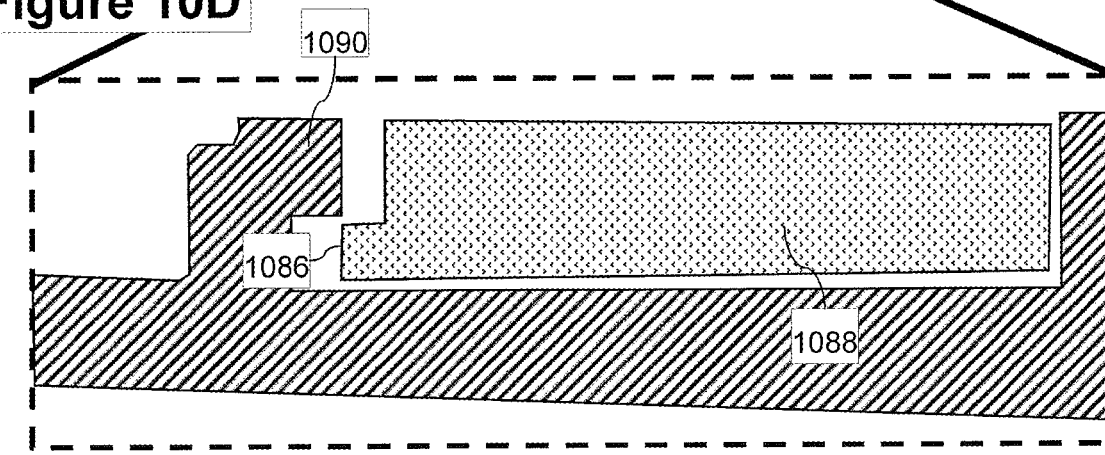

FIGS. 10A,B,B' illustrate a cutaway side view of an exemplary embodiment of a locking mechanism. FIG. 10B shows a close-up cutaway view of the exemplary locking mechanism in a permanently locked state. FIG. 10B' shows a close-up cutaway view of the exemplary locking mechanism in a temporarily locked state. FIG. 10C illustrates an overhead view of the exemplary infuser. FIG. 10D shows a cutaway overhead view of the infuser in a temporarily locked state. FIG. 10D' shows a cutaway overhead view of the infuser in a released state. FIG. 10D" shows a cutaway overhead view of the infuser in a permanently locked state.

In some embodiments, the locking mechanism may include a door 1026 and/or a permanent latch 1086 and/or a temporary latch 1088 and/or a catch 1084a for temporary latch 1088 and/or a catch 1084b for permanent latch 1086.

In the exemplary embodiment of FIGS. 10A-D, door 1026 opens by swinging upward. In the locked state, (for example as illustrated in FIGS. 10A,B,B' and D) catches 1084a and/or 1084b block respective latches 1088 and/or 1086 from moving upward, thereby preventing opening of door 1026.

In some embodiments, a user may a temporary latch from its latched state (for example the latched state of FIGS. 10B',D). For example, temporary latch 1088 may be released by pushing inward on a tab on the side of door 1026 (for example as illustrated by the arrow in FIG. 10D'). Pushing the side inward may, for example, move latches 1086 and/or 1088 inward away from catches 1084a,b freeing door 1026 to swing upward.

In some embodiments, activating a drive train 1056 (see FIG. 10A) causes drive train 1056 to push backwards against door 1026 (for example as illustrated by the arrow of FIG. 10A,B,D"). Backwards motion of door 1026 may (as illustrated by the arrows in FIGS. 10B and 10D") drive backwards, permanent latch 1086. In the backwards position latch 1086 is trapped by a block 1090. Block 1090 prevents latches 1086 and 1088 from moving sidewardly inward, preventing release of door 1026.

Figure 11A:
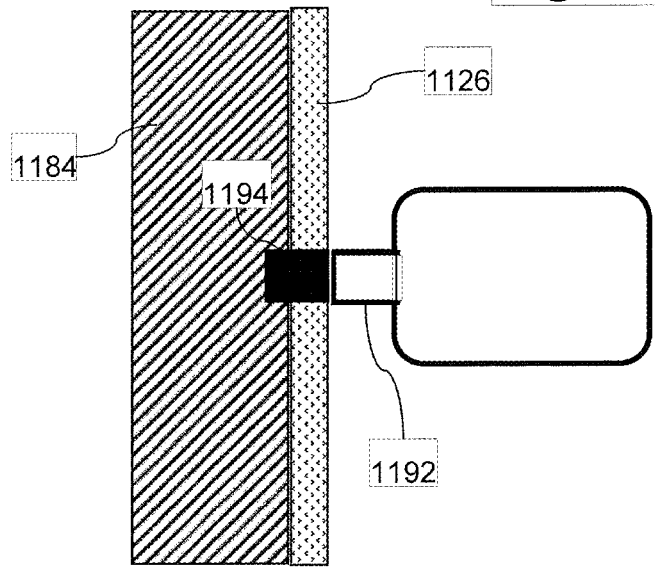
FIGS. 11A,B illustrate door locking bolt activated by a medicine discharge mechanism in accordance with an embodiment of the present invention.
Figure 11B:
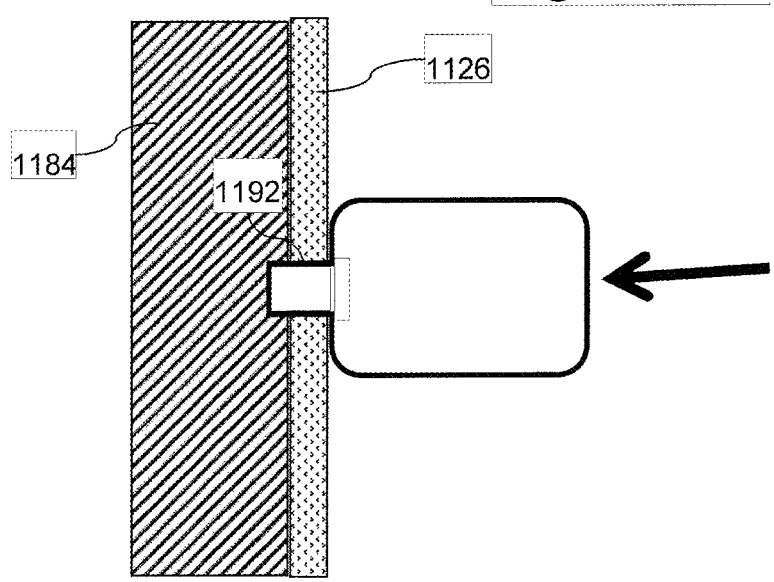

FIGS. 11A,B illustrate another alternate exemplary embodiment of a locking mechanism in an unlocked and locked position respectively. In some embodiments, a bolt 1192 may optionally be located along the path of motion of a drive train (not shown). Bolt 1192 may be pushed by the drive train into a hole 1194. Once inside hole 1194 bolt 1192 prevents a door 1126 from moving with respect to a hole 1194 thereby locking door 1126 in a closed state.

Figure 12A:
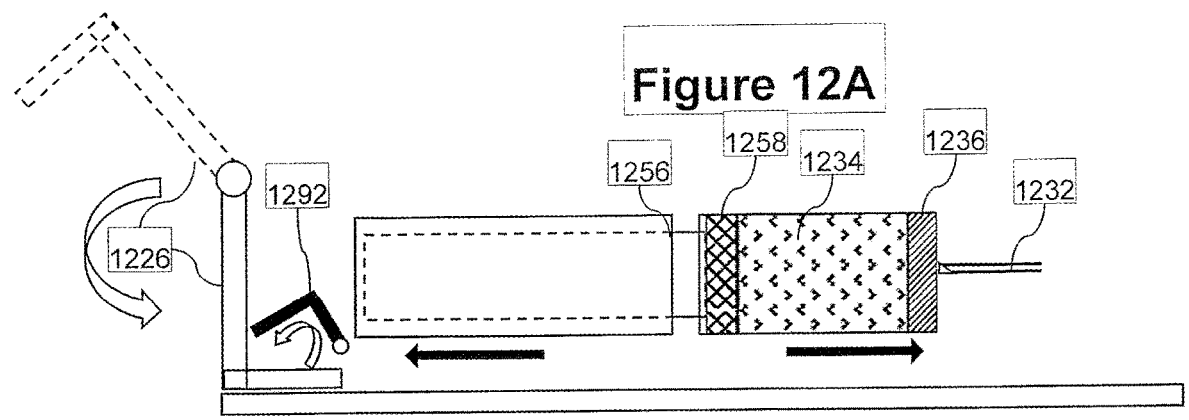
FIGS. 12A-C illustrate a schematic embodiment of an infuser having a septum puncturing mechanism and a locking mechanism in accordance with an embodiment of the present invention.
Figure 12B:
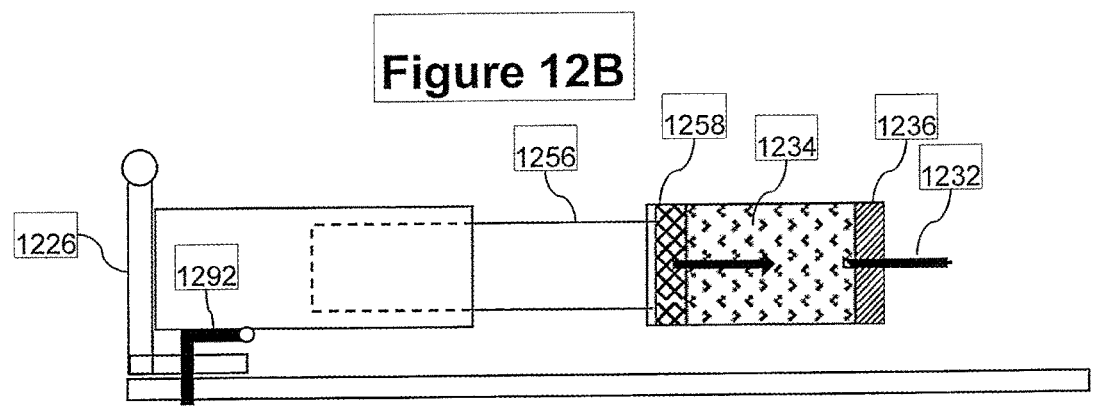
Figure 12C:
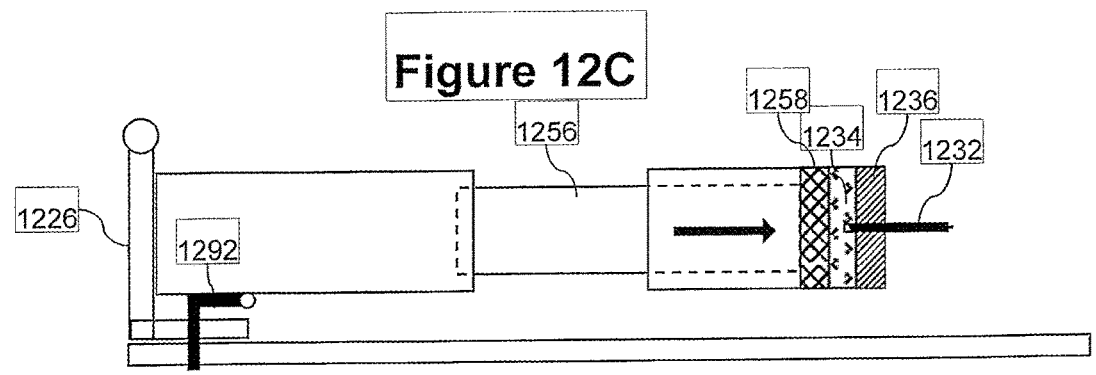

FIG. 12A-C illustrate an exemplary schematic embodiment of an infuser having a preliminary door lock and a preliminary unsealing mechanism. In the exemplary embodiment, the infuser includes a reservoir in a chamber. Access to the chamber is controlled by a door. The cartridge optionally includes a mechanical drive train, which can expand linearly. The door and/or the locking mechanism and/or the reservoir and/or a plunger and/or a seal and/or an unsealing mechanism may optionally be lined up along a path of motion of the drive train. Preliminary expansion of the drive train may prime the apparatus. For example, expansion of the drive train may drive the cartridge against the door locking mechanism thereby locking the door and/or expansion of the drive train may drive the cartridge against a seal breaking mechanism thereby unsealing the reservoir. After unsealing the reservoir and/or locking the door, further movement of the drive train may optionally drive the plunger into the reservoir dispensing the medicine.

FIG. 12A shows the exemplary embodiment of an infuser in an unprimed configuration. In the unprimed configuration a telescoping drive train 1256 is in a collapsed state. The user closes an access door 1226 and activates drive train 1256.

As drive train 1256 expands, it optionally pushes a rear end of drive train 1256. Drive train 1256 may, for example expand rearward. A locking mechanism including a rotating bolt 1292 is optionally situated along the path of motion of the drive train 1256. As drive train 1256 expands it optionally contacts bolt 1292 optionally rotating bolt 1292 to lock door 1226 closed (as can be seen for example in FIG. 12B). Optionally, if door 1226 is open a warning may be issued and/or the infuser may not function. Optionally drive train 1256 continues to expand pushing the rear end of drive train 1256 backwards until it optionally contacts the locked door 1226. Door 1226 may optionally stop rearward progress.

With the rear end of drive train 1256 blocked by door 1226, further, expansion of drive train 1256 optionally pushes the front end of drive train 1256 forward. A plunger 1258 is optionally situated along the path of motion of drive train 1256. As long as reservoir 1234 is sealed, plunger 1258 does not enter reservoir 1234. As long as reservoir 1234 is sealed, plunger 1258 pushes reservoir 1234 forward. A seal 1236 of reservoir 1234 is optionally pushed forward along a path of motion or drive train 1256 until it contacts an unsealing mechanism 1232 Unsealing mechanism, 1232 may optionally be situated along the line of motion of drive train 1256. For example, seal 1236 may include a septum and unsealing mechanism 1232 may include a hollow needle directed along the path of motion and pointed toward the septum. For example, drive train 1256 may drive the needle through the septum breaking the seal and/or creating a path for discharging the medicine (for example through the hollow of the needle). Locking the door and/or breaking the seal may optionally place the infuser into a primed state (for example as illustrated in FIG. 12B).

Once the infuser is primed, further expansion of drive train 1256 may drive plunger 1258 into reservoir 1234, discharging the medicine.

General

It is expected that during the life of a patent maturing from this application many relevant technologies will be developed and the scope of the terms is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A drug delivery device for delivering a drug to a recipient comprising:
    a housing including therein:
    a mechanical drive train, a reservoir containing said drug, a seal sealing an opening in the reservoir, a hollow needle for puncturing through the seal and unsealing the reservoir, and a plunger movably positioned in the reservoir,
    wherein, an initial movement of the drive train drives one of the hollow needle and the seal toward the other of the hollow needle and the seal, to, in turn, penetrate through the seal with the hollow needle and unseal the reservoir, and subsequent movement of the drive train advances the plunger through the reservoir, to, in turn, discharge the drug from the reservoir, and
    the housing further includes a base for attachment to the recipient, an opening for accessing the reservoir, a door movable between a closed position, at least partially blocking said opening, and an open position, unblocking said opening, and a locking mechanism for locking the door in the closed position, wherein the locking mechanism is activated by the initial movement of the drive train.

2. The drug delivery device of claim 1, further including a cartridge insertable into the housing, the reservoir being included in the cartridge.

3. The drug delivery device of claim 1, wherein the locking mechanism comprises a catch attached to one of the housing and the door, and a complementary latch attached to the other of the housing and the door, wherein the latch is biased away, and disengaged, from the catch in an unlocked position of the locking mechanism, and, when the door is in the closed position, the initial movement of the drive train drives the latch into engagement with the catch, in a locked position of the locking mechanism, to, in turn, lock the door closed.

4. The drug delivery device of claim 3, wherein the latch is spaced between about 0.1 mm and about 3 mm from the catch in the unlocked position of the locking mechanism.

5. The drug delivery device of claim 1, wherein the locking mechanism comprises a temporary catch attached to the housing and a complementary temporary latch attached to the door, wherein, when the door is in the closed position, the temporary latch engages the temporary catch, thereby holding the door in the closed position, and the temporary latch is manually disengageable from the temporary catch to move the locking mechanism into an unlocked position, allowing movement of the door from the closed position to the open position.

6. The drug delivery device of claim 1, wherein the locking mechanism further comprises a permanent catch attached to the housing and a complementary permanent latch attached to the door, wherein, when the door is in the closed position, the initial movement of the drive train drives the permanent latch into irreversible engagement with the permanent catch, in a permanent locked position of the locking mechanism, to, in turn, permanently lock the door closed.

7. The drug delivery device of claim 1, wherein the locking mechanism comprises a bolt extending along a pathway of the drive train, attached to one of the housing and the door, and a complementary slot extending along the pathway of the drive train, attached to the other of the housing and the door, wherein the bolt is disengaged, from the slot in an unlocked position of the locking mechanism, and when the door is in the closed position, the initial movement of the drive train drives the bolt into engagement with the slot, in a locked position of the locking mechanism, to, in turn, lock the door closed.

8. The drug delivery device of claim 1, wherein the locking mechanism comprises a bolt pivotably attached to the housing, and a complementary slot situated in the door, wherein the bolt is rotatable between an unlocked position, wherein the bolt is situated along a pathway of the drive train and not engaging the slot, and a locked position, engaging the slot, and, wherein, when the door is in the closed position, the movement of the drive train contacts the bolt in the unlocked position and rotates the bolt into the locked position, into engagement with the slot, to, in turn, lock the door closed.

9. A method for delivering a drug to a recipient via a drug delivery device, the drug delivery device including a housing including therein a mechanical drive train, a reservoir containing said drug, a seal for sealing the reservoir, a hollow needle, and a plunger, the housing further including a base, an opening for accessing the reservoir, a door, and a locking mechanism, the method comprising:

attaching the base to the recipient;
moving the door into a closed position, at least partially blocking the opening;
initially driving the mechanical drive train, and, in turn, activating the locking mechanism to lock the door in the closed position and driving one of the hollow needle and the seal toward the other of the hollow needle and the seal, and, in turn, penetrating through the seal with the hollow needle to unseal the reservoir, and
further driving the mechanical drive train to advance the plunger through the reservoir, and, in turn, discharge the drug from the reservoir.

10. The method of claim 9, wherein the reservoir is contained in a cartridge and the method further comprising inserting the cartridge through the opening into housing prior to the moving step.

11. The method of claim 9, further comprising rotating a gear and, in turn, powering the driving of the mechanical drive train.

12. The method of claim 9, wherein the locking mechanism comprises a catch attached to one of the housing and the door, and a complementary latch attached to the other of the housing and the door, wherein the latch is biased away, and disengaged, from the catch in an unlocked position of the locking mechanism, and wherein the step of activating the locking mechanism comprises driving the latch into engagement with the catch.

13. The method of claim 9, wherein the locking mechanism comprises a temporary catch attached to the housing and a complementary temporary latch attached to the door, and, wherein the step of moving the door into the closed position comprises engaging the temporary latch with the temporary catch.

14. The method of claim 13, wherein the temporary latch is manually disengageable from the temporary catch for moving the door from the closed position to an open position, prior to the initial driving of the mechanical drive train.

15. The method of claim 13, wherein the locking mechanism further comprises a permanent catch attached to the housing and a complementary permanent latch attached to the door, and wherein the step of activating the locking mechanism comprises driving the permanent latch into irreversible engagement with the permanent catch.

16. The method of claim 9, wherein the locking mechanism comprises a bolt extending along a pathway of the drive train, attached to one of the housing and the door, and a complementary slot extending along the pathway of the drive train, attached to the other of the housing and the door, and wherein the step of activating the locking mechanism comprises driving the bolt into engagement with the slot.

17. The apparatus of claim 9, wherein the locking mechanism comprises a bolt pivotably attached to the housing, and a complementary slot situated in the door, and wherein the initial driving step comprises contacting and rotating the bolt and the step of activating the locking mechanism comprises rotating the bolt into engagement with the slot.

* * * * *